(12) United States Patent
Saga

(10) Patent No.: US 9,327,417 B2
(45) Date of Patent: May 3, 2016

(54) CUTTER APPARATUS FOR WORKPIECE OF ABSORBENT ARTICLE

(75) Inventor: Tomoyuki Saga, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 393 days.

(21) Appl. No.: 13/808,144

(22) PCT Filed: Jul. 6, 2011

(86) PCT No.: PCT/JP2011/065474
§ 371 (c)(1),
(2), (4) Date: Mar. 18, 2013

(87) PCT Pub. No.: WO2012/008341
PCT Pub. Date: Jan. 9, 2012

(65) Prior Publication Data
US 2013/0160626 A1 Jun. 27, 2013

(30) Foreign Application Priority Data

Jul. 12, 2010 (JP) ................ 2010-158087

(51) Int. Cl.
*B23D 25/12* (2006.01)
*B26D 1/40* (2006.01)
(Continued)

(52) U.S. Cl.
CPC .......... *B26D 1/405* (2013.01); *A61F 13/15723* (2013.01); *B26D 7/265* (2013.01);
(Continued)

(58) Field of Classification Search
CPC .......... B26D 1/405; B26D 7/265; B26D 5/12; B26D 7/20; B26D 7/2628; A61F 13/15723; A61F 2013/15918; B26F 1/384; Y10T 83/4838; Y10T 83/4833; B65H 2301/121; B65H 35/08; B21B 39/006; B21B 13/10; B21B 2027/022; B21B 31/16; B21B 31/18
USPC ........... 83/344–346, 658–663, 100, 506, 649, 83/887; 225/10, 106
See application file for complete search history.

(56) References Cited

U.S. PATENT DOCUMENTS 3,908,426 A * 9/1975 Aramaki ......................... 72/238
4,119,256 A * 10/1978 Vogtmann et al. ............ 226/177
(Continued)

FOREIGN PATENT DOCUMENTS

| CN | 1662350 A | 8/2005 |
|---|---|---|
| CN | 1839020 A | 9/2006 |

(Continued)

OTHER PUBLICATIONS

International Search Report for PCT/JP2011/065474, dated Aug. 16, 2011.
(Continued)

*Primary Examiner* — Ghassem Alie
*Assistant Examiner* — Bharat C Patel
(74) *Attorney, Agent, or Firm* — Hauptman Ham, LLP

(57) ABSTRACT

A cutter apparatus for cutting a workpiece of an absorbent article that is being transported in a transport direction, includes: a cutter roller having a cutter blade projecting from an outer circumferential surface thereof; and an anvil roller that receives the cutter blade at an outer circumferential surface thereof disposed to face the outer circumferential surface of the cutter roller. While rotating mutually in the transport direction, the cutter roller and the anvil roller cut the workpiece by allowing the workpiece to pass between the rollers. In at least one of the cutter roller and the anvil roller, a dynamic-balance correction section is provided which corrects the dynamic balance of the roller so that the sum of the values of balance quality (mm/sec) defined in JIS B 0905 at one end and the other end of the roller in a rotational-axis direction is 6 or less.

11 Claims, 13 Drawing Sheets

(51) Int. Cl.
  *B26D 7/26* (2006.01)
  *B26F 1/38* (2006.01)
  *A61F 13/15* (2006.01)
  *B26D 5/12* (2006.01)
  *B26D 7/20* (2006.01)

(52) U.S. Cl.
  CPC ...... *B26F 1/384* (2013.01); *A61F 2013/15918* (2013.01); *B26D 5/12* (2013.01); *B26D 7/20* (2013.01); *Y10T 83/4838* (2015.04)

(56) References Cited

U.S. PATENT DOCUMENTS

| | | | | |
|---|---|---|---|---|
| 4,690,344 | A | * | 9/1987 | Yokota ........................ 242/564.1 |
| 4,759,485 | A | * | 7/1988 | Braun et al. ................... 226/176 |
| 4,920,627 | A | * | 5/1990 | Aikins et al. ................ 29/402.08 |
| 5,072,872 | A | * | 12/1991 | Casset et al. ................... 226/176 |
| 5,109,741 | A | * | 5/1992 | Fuchs .................. B26D 7/1863 83/100 |
| 5,388,490 | A | * | 2/1995 | Buck ............................... 83/880 |
| 5,778,782 | A | * | 7/1998 | Behringer et al. ............. 101/226 |
| 5,957,826 | A | * | 9/1999 | Bohn ................... B26D 7/2614 493/354 |
| 6,009,781 | A | * | 1/2000 | McNeil .................. B26D 1/405 83/304 |
| 7,594,461 | B2 | * | 9/2009 | Aichele et al. ................... 83/344 |
| 2004/0003699 | A1 | * | 1/2004 | Welch ............................. 83/658 |
| 2007/0039443 | A1 | * | 2/2007 | Takahashi et al. .............. 83/659 |
| 2009/0320663 | A1 | * | 12/2009 | Yamamoto ...................... 83/100 |

FOREIGN PATENT DOCUMENTS

| | | |
|---|---|---|
| EP | 0963821 A1 | 12/1999 |
| EP | 1658940 A1 | 5/2006 |
| JP | 6-312400 A | 11/1994 |
| JP | 11-23993 A | 1/1999 |
| JP | 11-023993 A | 1/1999 |
| JP | 11-188699 A | 7/1999 |
| JP | 2002-096290 A | 4/2002 |
| JP | 2005-532183 A | 10/2005 |
| JP | 2006-239815 A | 9/2006 |
| JP | 2010-013196 A | 1/2010 |
| JP | 2010-13196 A | 1/2010 |
| JP | 2010-137271 A | 6/2010 |
| WO | 2005021224 A1 | 3/2005 |

OTHER PUBLICATIONS

Extended European Search Report issued Oct. 27, 2014, corresponding to European patent application No. 11806671.1.
Office Action dated Aug. 7, 2015, corresponding to European patent application No. 11806671.1.
Office Action issued Apr. 28, 2015, corresponding to Eupopean patent application No. 11806671.1.

* cited by examiner

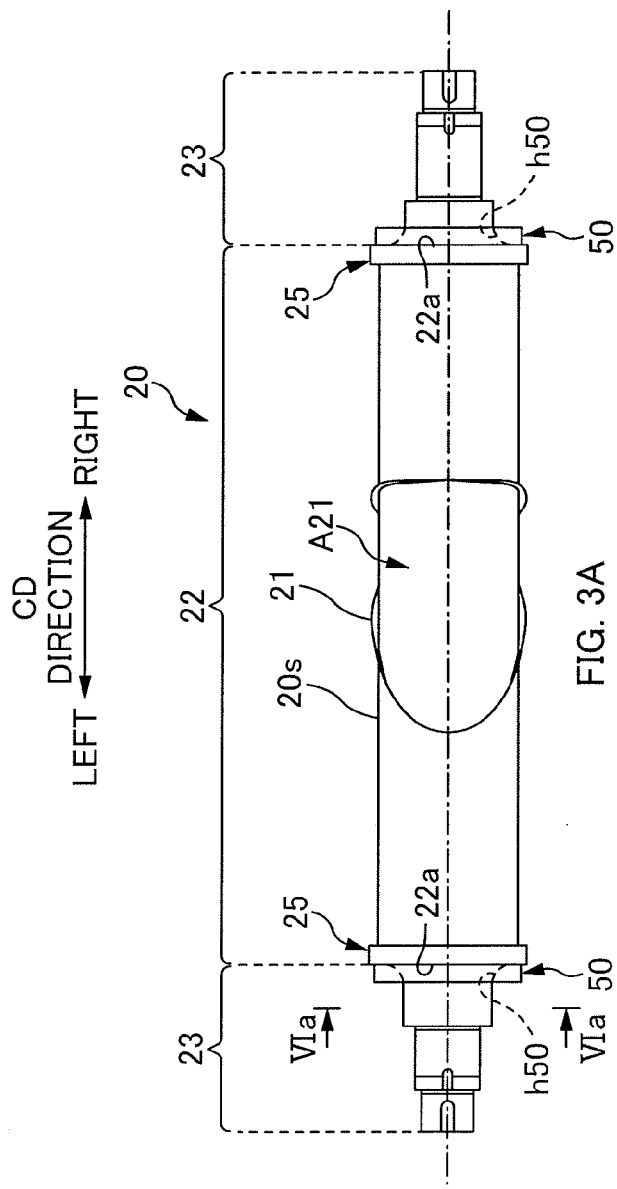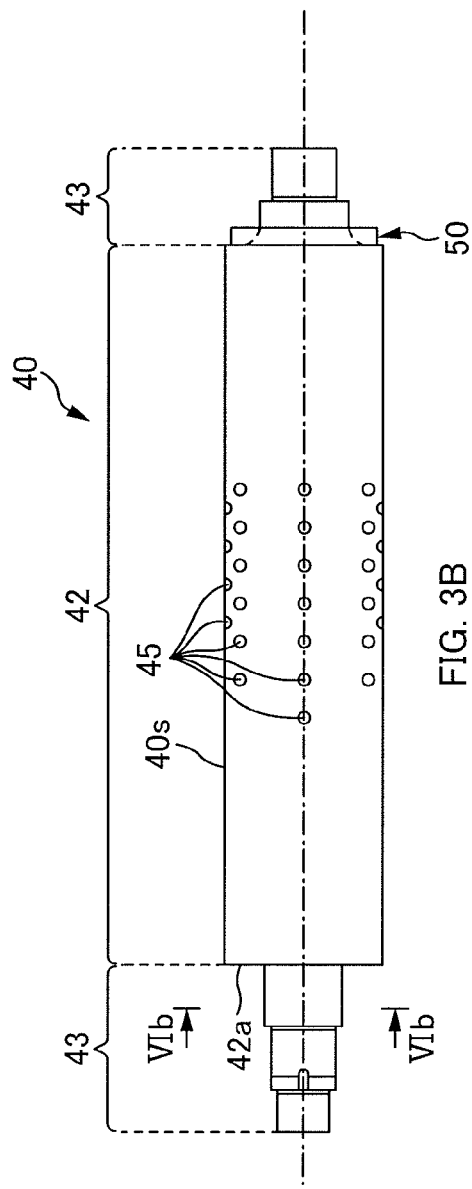

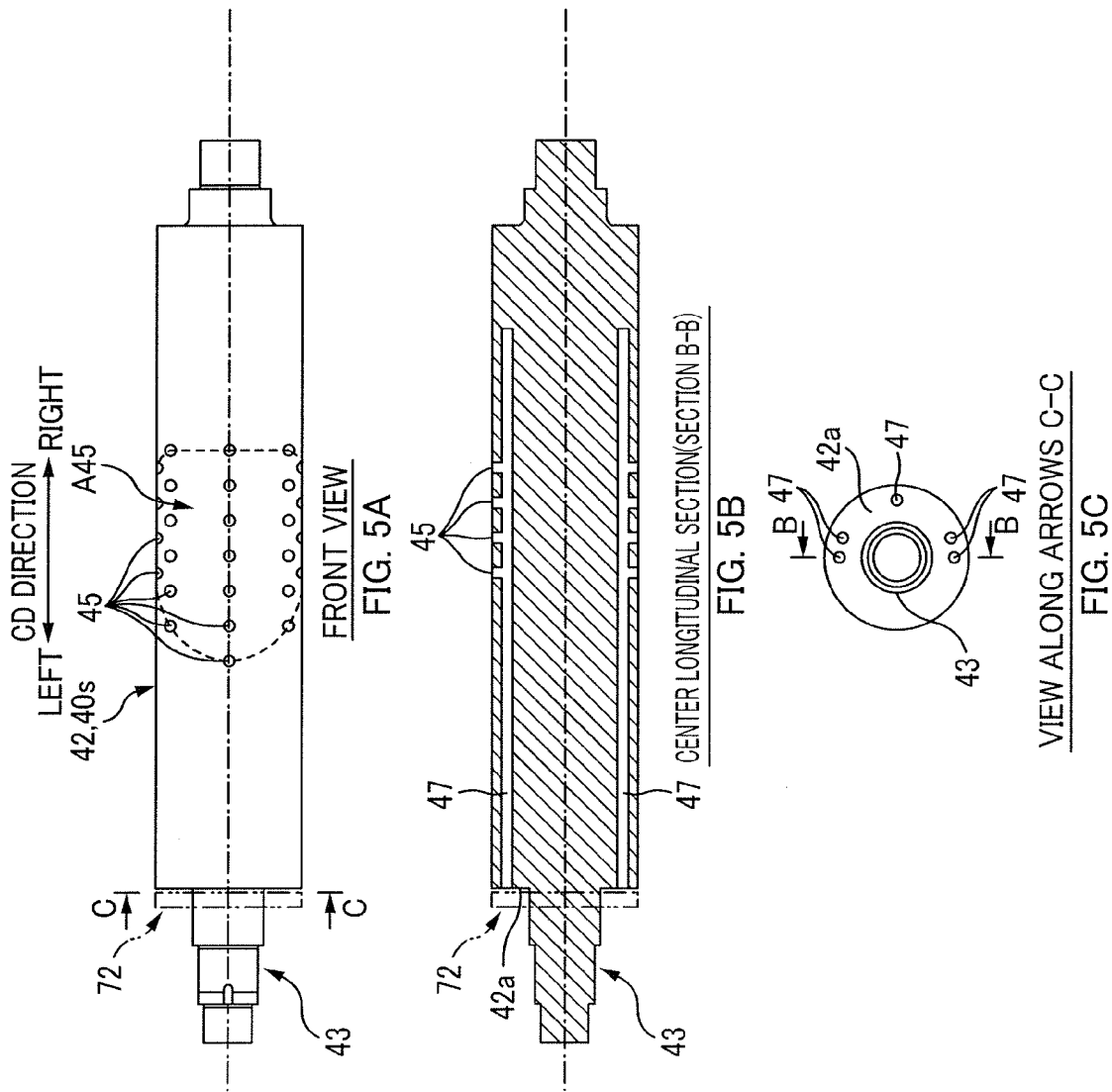

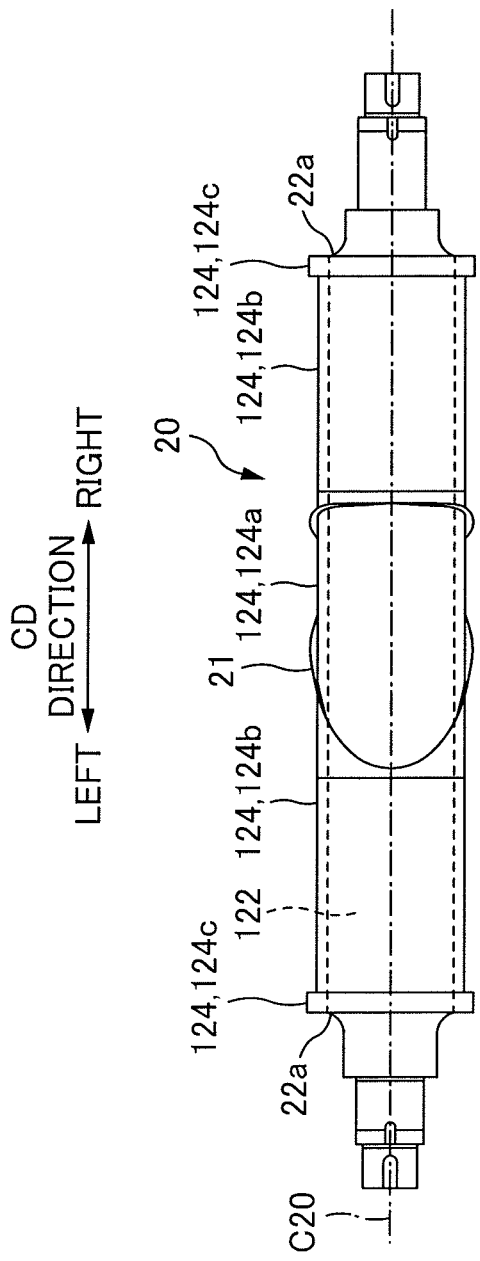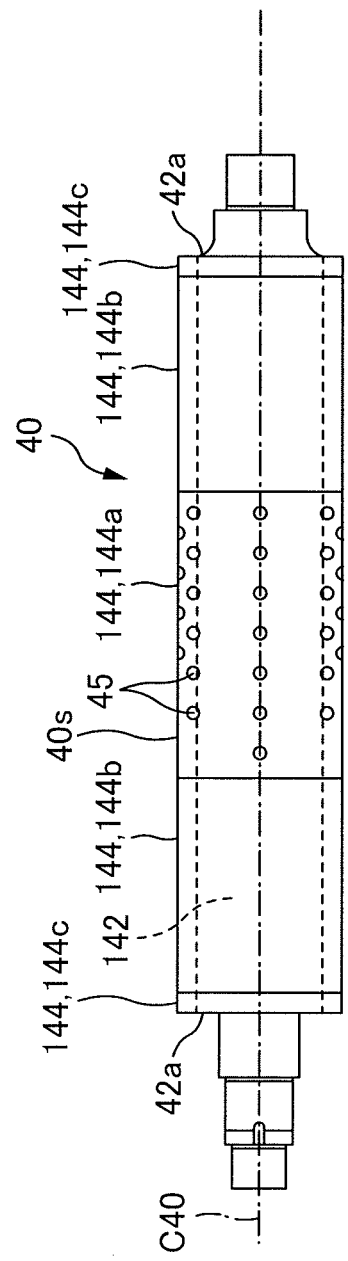

TABLE 1

| NAME | ROLLER MASS [kg] | ROTATIONAL SPEED [rpm] | L RESIDUAL UNBALANCE AMOUNT [kg] (UNBALANCE POSITION) | L BALANCE CORRECTION RADIUS (mm) | L BALANCE QUALITY [mm/s] | R RESIDUAL UNBALANCE AMOUNT [kg] (UNBALANCE POSITION) | R BALANCE CORRECTION RADIUS (mm) | R BALANCE QUALITY [mm/s] | SUM OF BALANCE QUALITY [mm/s] | BLADE LIFE [TEN THOUSAND pc.] |
|---|---|---|---|---|---|---|---|---|---|---|
| CUTTER ROLLER | 270 | 200 | 0.133 (35.5°) | 95 | 0.98 | 0.095 (356°) | 95 | 0.7 | 1.68 | 200 |
| ANVIL ROLLER | 300 | 200 | 1.203 (173°) | 95 | 7.98 | 0.605 (17.5°) | 95 | 4.01 | 11.99 | |

TABLE 2

| NAME | ROLLER MASS [kg] | ROTATIONAL SPEED [rpm] | L RESIDUAL UNBALANCE AMOUNT [kg] (UNBALANCE POSITION) | L BALANCE CORRECTION RADIUS (mm) | L BALANCE QUALITY [mm/s] | R RESIDUAL UNBALANCE AMOUNT [kg] (UNBALANCE POSITION) | R BALANCE CORRECTION RADIUS (mm) | R BALANCE QUALITY [mm/s] | SUM OF BALANCE QUALITY [mm/s] | BLADE LIFE [TEN THOUSAND pc.] |
|---|---|---|---|---|---|---|---|---|---|---|
| CUTTER ROLLER | 270 | 200 | 0.133 (35.5°) | 95 | 0.98 | 0.095 (356°) | 95 | 0.7 | 1.68 | 1,300 |
| ANVIL ROLLER | 300 | 200 | 0.651 (174°) | 95 | 4.32 | 0.273 (174°) | 95 | 1.81 | 6.13 | |

TABLE 3

| NAME | ROLLER MASS [kg] | ROTATIONAL SPEED [rpm] | L RESIDUAL UNBALANCE AMOUNT [kg] (UNBALANCE POSITION) | L BALANCE CORRECTION RADIUS (mm) | L BALANCE QUALITY [mm/s] | R RESIDUAL UNBALANCE AMOUNT [kg] (UNBALANCE POSITION) | R BALANCE CORRECTION RADIUS (mm) | R BALANCE QUALITY [mm/s] | SUM OF BALANCE QUALITY [mm/s] | BLADE LIFE [TEN THOUSAND pc.] |
|---|---|---|---|---|---|---|---|---|---|---|
| CUTTER ROLLER | 270 | 200 | 0.005 (310°) | 95 | 0.037 | 0.0005 (3°) | 95 | 0.0037 | 0.04 | 1,400 |
| ANVIL ROLLER | 300 | 200 | 0.164 (172°) | 95 | 1.09 | 0.0043 (210°) | 95 | 0.029 | 1.12 | |

FIG. 9

TABLE 4

| PRESENCE OF TEST WEIGHT | L-SIDE MEASURED DATA | | | R-SIDE MEASURED DATA | | |
|---|---|---|---|---|---|---|
| | SYMBOL | AMPLITUDE | PHASE | SYMBOL | AMPLITUDE | PHASE |
| NONE ON BOTH SIDES | L0 | 4 μm | 20° | R0 | 6 μm | 300° |
| ONLY L SIDE 5g∠0° | L1 | 6 μm | 110° | R1 | 4 μm | 210° |
| ONLY R SIDE 5g∠0° | L2 | 8 μm | 290° | R2 | 2 μm | 3° |

FIG. 13

CUTTER APPARATUS FOR WORKPIECE OF ABSORBENT ARTICLE

RELATED APPLICATIONS

The present application is National Phase of International Application Number PCT/JP2011/065474, filed Jul. 6, 2011, and claims priority from Japanese Application Number 2010-158087, filed Jul. 12, 2010.

TECHNICAL FIELD

The present invention relates to a cutter apparatus that cuts a workpiece of an absorbent article such as a disposable diaper.

BACKGROUND ART

Conventionally, in a production line for an absorbent article such as disposable diapers, while a workpiece made of nonwoven fabric, etc. is transported in a transport direction, the workpiece is partially punched (removed), cut, or separated into each product. In short, the workpiece is cut. This processing is performed by a rotary die cutter apparatus.

The cutter apparatus has a cutter roller that includes a cutter blade projecting from the outer circumferential surface, and a smooth anvil roller that receives the cutter blade. While the cutter roller and the anvil roller are rotating in the transport direction of the workpiece, the workpiece passes through a nip between the rollers. As a result, the workpiece is cut.

Such a cutter apparatus has bearers in some cases. The bearers are ring-shaped projecting portions that project in the shape of rings along the circumferential direction at both end portions of the outer circumferential surface of the cutter roller. The bearers have a function of transmitting a rotational torque from one roller to the other roller by coming into contact with the outer circumferential surface of the anvil roller.

In such a cutter apparatus, a cut error (cutting failure) occurs in the following cases: when a clearance is produced between a cutter edge of the cutter blade and the anvil roller due to deformation of the cutter edge such as wear, chipping, etc.; or when a cutting load large enough to cut the workpiece is no more imposed on the workpiece due to wear of the cutter edge.

In the past, various techniques for preventing such a cut error have been proposed.

For example, Patent Document 1 describes a technique for preventing wear and chipping due to collision of the cutter edge against the anvil roller: an idle blade that does not contribute to cutting is provided at a position where the cutter blade is discontinuous in the rotational direction of the cutter roller, whereby stress concentration on a portion neighboring the discontinuous position of the cutter blade at the time of cutting is relieved or reduced.

Also, Patent Document 2 describes a technique for preventing cutting failure caused by flexure of the cutter roller and the anvil roller: a direct-press roller is pressed from above against the bearers of the cutter roller that is the upper roller, and a direct-press roller is pressed from below against the anvil roller that is the lower roller, whereby flexure of the rollers at the time of cutting is reduced to maintain good cutting sharpness.

Further, Patent Document 3 describes a technique for preventing cutting failure caused by thermal expansion of the bearers, in which grooves for heat dissipation are formed on the outer circumferential surface of the bearers.

CITATION LIST

Patent Document

Patent Document 1: P H11-188699A
Patent Document 2: JP 2002-96290A
Patent Document 3: JP 2006-239815A

SUMMARY OF INVENTION

Technical Problem

With the recent speedup in the production facilities for an absorbent article, however, a new problem has occurred in which degradation in the durability of the cutter blade cannot be prevented effectively even using the techniques described above. This problem is related to rotational vibration occurring due to failure in dynamic balancing of the roller, which previously did not become so evident for reasons such as that the production speed was low and thus the rotational speed of the roller was low.

With increase in the rotational speed of the roller along with the speedup in the production facilities as described above, rotational vibration-caused chipping and wear of the cutting edge have become easy to occur. Also, recently, with the proliferation of diapers for adults, production facilities that use very large rollers have increased. Since such rollers are heavy, the rotational vibration may further be promoted and expanded.

In view of the conventional problem described above, it is an objective of the present invention to suppress or reduce rotational vibration of a roller, to achieve extension of the life of the cutter blade.

Solution to Problem

In order to address the above-described problem, a primary aspect of the invention is a cutter apparatus for cutting a workpiece of an absorbent article that is being transported in a transport direction, including:

a cutter roller that has a cutter blade projecting from an outer circumferential surface of the cutter roller;

an anvil roller that receives the cutter blade on an outer circumferential surface of the anvil roller disposed to face the outer circumferential surface of the cutter roller, the cutter roller and the anvil roller cutting the workpiece by allowing the workpiece to pass between the cutter roller and the anvil roller while the cutter roller and the anvil roller are both rotating in the transport direction; and a dynamic-balance correction section that, for at least one roller of the cutter roller and the anvil roller, corrects the dynamic balance of the at least one roller so that a sum of values of balance quality at one end and another end of the at least one roller in a rotational-axis direction is 6 or less, the balance quality (mm/sec) being defined in JIS B 0905.

Features of the invention other than the above will become clear by reading the description of the present specification with reference to the accompanying drawings.

Advantageous Effects of Invention

According to the present invention, the rotational vibration of a roller can be suppressed or reduced, to achieve extension of the life of a cutter blade.

BRIEF DESCRIPTION OF DRAWINGS

FIG. 2 is a schematic top view showing how the cutter apparatus 10 punches a semi-finished product 1a.

FIGS. 3A and 3B are front views of a cutter roller 20 and an anvil roller 40, respectively.

FIG. 5A is a front view of the anvil roller 40 for describing a collection mechanism 70, FIG. 5B is a center longitudinal sectional view of the anvil roller 40 (a sectional view taken along line B-B in FIG. 5C), and FIG. 5C is a view along arrows C-C in FIG. 5A.

FIG. 7A is a front view of the cutter roller 20 for describing a dynamic balance correction method, and FIG. 7B is a front view of the anvil roller 40.

FIG. 9 shows Tables 1 to 3 of experiment standards for experiments for examining the relationship between the balance quality and the life of a cutter blade 21.

FIG. 13 shows Table 4 of measurement data used for calculation of the correction weights $W_{cL}$ and $W_{cR}$, in order to describe an example of calculation.

DESCRIPTION OF EMBODIMENTS

Figure 1:
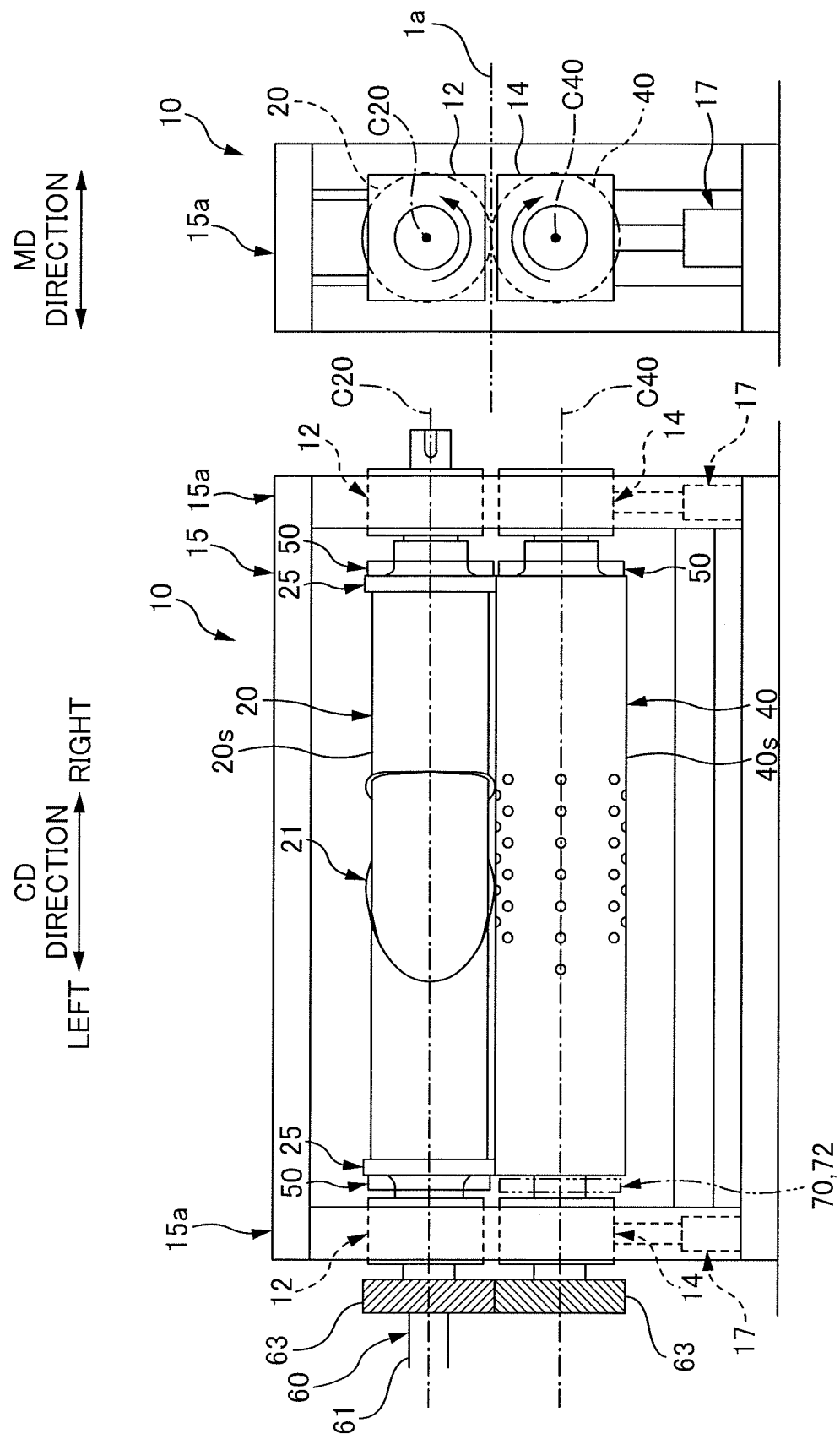
FIG. 1A is a schematic front view of a cutter apparatus 10 of an embodiment.
FIG. 1B is a side view thereof.

At least the following matters will be made clear by the explanation in the present specification and the description of the accompanying drawings.

A cutter apparatus for cutting a workpiece of an absorbent article that is being transported in a transport direction, including:

a cutter roller that has a cutter blade projecting from an outer circumferential surface of the cutter roller;

an anvil roller that receives the cutter blade on an outer circumferential surface of the anvil roller disposed to face the outer circumferential surface of the cutter roller, the cutter roller and the anvil roller cutting the workpiece by allowing the workpiece to pass between the cutter roller and the anvil roller while the cutter roller and the anvil roller are both rotating in the transport direction; and a dynamic-balance correction section that, for at least one roller of the cutter roller and the anvil roller, corrects the dynamic balance of the at least one roller so that a sum of values of balance quality at one end and another end of the at least one roller in a rotational-axis direction is 6 or less, the balance quality (mm/sec) being defined in JIS B 0905.

According to the cutter apparatus for cutting a workpiece of an absorbent article described above, at least one roller is subjected to dynamic balance correction so that the sum of the values of balance quality is 6 or less. Therefore, the rotation vibration of the roller can be considerably reduced, to achieve extension of the life of the cutter blade.

In the cutter apparatus for a workpiece of an absorbent article described above, it is desirable that the apparatus further comprises a dynamic-balance correction section that, for both of the cutter roller and the anvil roller, corrects the dynamic balance of one or both of the rollers so that the sum of values of balance quality at one end and another end of each of the rollers in the rotational-axis direction is 6 or less, the balance quality being defined in JIS B 0905.

According to the cutter apparatus for a workpiece of an absorbent article described above, the sum of the values of balance quality is 6 or less for both the cutter roller and the anvil roller. Therefore, the rotation vibration of both rollers can be considerably reduced, and thus the life of the cutter blade can be extended without fail.

In the cutter apparatus for a workpiece of an absorbent article described above, it is desirable that the cutter roller and the anvil roller are arranged vertically, a rotational direction in which the cutter roller rotates about its rotational axis is opposite to a rotational direction in which the anvil roller rotates about its rotational axis, both the cutter roller and the anvil roller have their respective predetermined reference positions facing each other on their respective outer circumferential surfaces, positions on each of the cutter roller and the anvil roller along their respective rotational direction corresponds to 0° to 360° rotational-angular positions from their respective start positions which are the predetermined reference positions, when cutting the workpiece by allowing the workpiece to pass between the cutter roller and the anvil roller, the cutter roller and the anvil roller are rotated so that their rotational-angular positions match with each other, the values of the balance quality at the one end and the other end are calculated based on residual unbalance amounts measured using a two-plane balancing machine defined in JIS B 7737, and assuming that the one of the cutter roller and the anvil roller is a first roller and the other roller is a second roller, both an unbalance position related to the residual unbalance amount at one end of the first roller and an unbalance position related to the residual unbalance amount at the other end of the first roller fall within a range of 90° to 270° rotational-angular positions, and both an unbalance position related to the residual unbalance amount at one end of the second roller and an unbalance position related to the residual unbalance amount at the other end of the second roller fall within a range of 270° to 360° or 0° to 90° rotational-angular positions.

According to the cutter apparatus for a workpiece of an absorbent article described above, the directions of the centrifugal force caused by the residual unbalance amounts of the rollers can be made substantially the same. In other words, when the direction of the centrifugal force caused by the residual unbalance amounts of the cutter roller is upward, the direction of the centrifugal force caused by the residual unbalance amounts of the anvil roller is also substantially upward. Also, when the direction of the centrifugal force caused by the residual unbalance amounts of the cutter roller is downward, the direction of the centrifugal force caused by the residual unbalance amounts of the anvil roller is also substantially downward. This makes it easy to keep the distance between the cutter roller and the anvil roller substantially constant. Therefore, a phenomenon such as periodic strong bumps of the rollers at a given rotational-angular position becomes less likely to occur. Thus, the cutting load can be made uniform over the entire circumference of the cutter roller. As a result, local wear, etc. on the cutter blade and the outer circumferential surface of the anvil roller is effectively suppressed or reduced, and thus extension of the life of the cutter blade can be achieved.

In the cutter apparatus for a workpiece of an absorbent article described above, it is desirable that the roller whose dynamic balance is to be corrected has a surface-layer section and a core section that is located more inside than the surface-layer section, the surface-layer section and the core section being made of different materials from each other, a hardness of the surface-layer section is higher than a hardness of the core section, and an end face of the core section in a direction along the rotational axis has a hole that serves as the dynamic-balance correction section, and the dynamic balance of the roller is corrected by forming the hole.

According to the cutter apparatus for a workpiece of an absorbent article described above, the dynamic balance can be easily corrected by forming a hole on an end face of the core section low in hardness.

In the cutter apparatus for a workpiece of an absorbent article described above, it is desirable that the cutting of the workpiece is to punch a part of the workpiece into a predetermined punched shape, the cutter blade defines a closed area on the outer circumferential surface of the cutter roller in correspondence with the punched shape, the roller whose balance is corrected by forming a hole on an end face thereof is the anvil roller, the anvil roller has a plurality of air vents for suction on an area of the outer circumferential surface of the anvil roller, the area facing the closed area of the cutter blade, and the anvil roller has an air flow path inside the anvil roller along the rotational axis so that an end face at one end of the anvil roller is connected to the air vents, the air flow path communicating with the air vents and sucking air from the air vents.

According to the cutter apparatus for a workpiece of an absorbent article described above, the advantages described above can be obtained effectively. The details are as follows. The anvil roller has the air vents and the air flow paths formed inside, which results in dynamic unbalance, causing the possibility of inducing a large rotational vibration. In addition, the ends of the air flow paths are disposed at an end face of the roller. Therefore, a disk-shaped balance weight which serves as the dynamic-balance correction section is attached to the end face of the roller, which might block the air flow paths and make it difficult to attach the balance weight to the end face. That is, the dynamic balance correction using a balance weight is difficult. However, according to the configuration described above, the core section at the end face of the anvil roller has low hardness and thus can be machined directly. Therefore, by the direct hole formation, the dynamic balance correction can be performed without use of a balance weight, and, as a result, the advantages described above can be obtained effectively.

Embodiment

Figure 2:
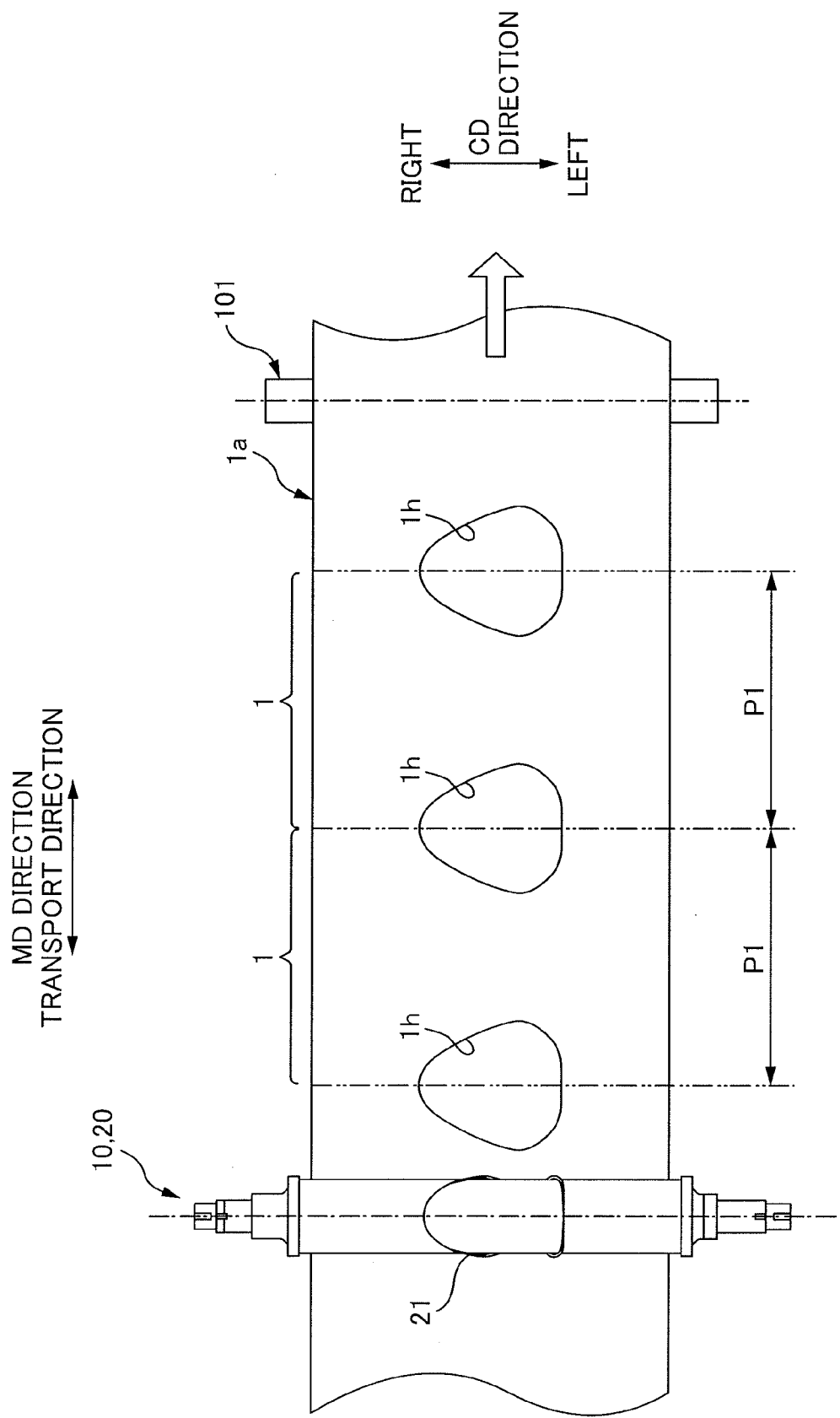

FIGS. 1A and 1B are explanatory views of a cutter apparatus 10 of an embodiment, where FIG. 1A is a schematic front view of the cutter apparatus 10, and FIG. 1B is a side view thereof. FIG. 2 is a schematic top view illustrating how the cutter apparatus 10 punches a semi-finished product 1a.

As shown in FIG. 2, the cutter apparatus 10 is used in a production line for pull-on disposable diapers 1 for adults which are an example of the absorbent article. In this example, the cutter apparatus 10 punches leg openings 1h of the diapers 1 at a product pitch P1 of the diapers 1 in the semi-finished product 1a (corresponding to a workpiece), the semi-finished product 1a being a soft continuous sheet-like member made of nonwoven fabric, etc. that is transported continuously in a transport direction.

However, the semi-finished product 1a is not limited to a continuous sheet-like member. That is to say, the semi-finished product 1a may be separated into units corresponding to the products of the diapers 1, and such separate units may be individually transported. In this case, as a transport mechanism for transporting the semi-finished products 1a, a suction conveyer (a belt conveyer having an adsorption function on its mount surface), etc. may be used in place of a transport roller 101. Also, the style of cutting of the semi-finished product 1a is not limited to punching. The continuous sheet-like member may be cut into products, or the semi-finished product 1a may be cut only partially.

In the following description, the transport direction of such a semi-finished product 1a is also referred to as an "MD direction," and, of the directions orthogonal to the MD direction, the direction that is not the thickness direction of the semi-finished product 1a (i.e., the width direction of the sheet-like member when the semi-finished product 1a is a continuous sheet-like member) is also referred to as a "CD direction." As for the CD direction, one side of the CD direction is also referred to as a left (L) side and the other side thereof is also referred to as a right (R) side.

As shown in FIGS. 1A and 1B, the cutter apparatus 10 includes: a cutter roller 20 as an upper roller that is supported by bearing members 12 in a rotatable manner about a rotational axis C20 parallel to the CD direction; an anvil roller 40 as a lower roller that is disposed below the cutter roller 20 and supported by bearing members 14 in a rotatable manner about a rotational axis C40 parallel to the CD direction; a drive mechanism 60 that drives rotation of the pair of upper and lower rollers 20 and 40; and a collection mechanism 70 that separates punched-out pieces of the semi-finished product 1a from the semi-finished product 1a and collects such pieces.

The leg openings 1h in the semi-finished product 1a is punched as follows: when the semi-finished product 1a (not shown in FIGS. 1A and 1B) passes along the MD direction through a nip between the cutter roller 20 and the anvil roller 40 that are mutually driven to rotate in the MD direction, the semi-finished product 1a is pinched by a cutter blade 21 on an outer circumferential surface 20s of the cutter roller 20 and an outer circumferential surface 40s of the anvil roller 40, the MD direction serving as the transport direction. The resultant punched-out pieces are separated from the semi-finished product 1a and discharged to the outside of the production line by the collection mechanism 70. Here, when the cutter roller 20 and the anvil roller 40 mutually rotate along the MD direction as described above, the rotational direction of the cutter roller 20 about the rotational axis C20 (the counterclockwise direction in the illustrated example) and the rotational direction of the anvil roller 40 about the rotational axis C40 (the clockwise direction in the illustrated example) are opposite to each other. The components 20, 40, 60, and 70 will be described hereinafter.

FIGS. 3A and 3B are front views of the cutter roller 20 and the anvil roller 40, respectively.

The cutter roller 20 includes: a roller-body section 22 that is the main body of the roller, and small-diameter sections 23 that are formed coaxially and project at both ends of the roller-body section 22 in the CD direction. The above-described bearing members 12 are respectively arranged on the small-diameter sections 23. The cutter blade 21 is disposed on the outer circumferential surface 20s of the roller-body section 22. The cutter blade 21 projects from the outer circumferential surface 20s, the cutter blade 21 having a shape corresponding to the shape of the leg openings 1h, which is the shape into which the sheet is to be punched. Therefore, the cutter blade 21 defines a closed area A21 corresponding to the shape of the leg opening 1h on the outer circumferential surface 20s. Hereinafter, this closed area A21 is also referred to as a cutter blade-defining area A21.

Moreover, the turning radius of the edge of the cutter blade 21 is set, for example, to a value substantially equal to a value obtained by dividing the product pitch P1 of the diapers 1 by $2\pi$ (twice the value of pi). Therefore, when the cutter roller 20 rotates once, the semi-finished product 1a moves in the MD direction by a length P1 corresponding to one product piece.

In some cases, bearers 25 may be provided on the outer circumferential surface 20s of the roller-body section 22, as shown in FIG. 3A. The bearers 25 are large-diameter sections respectively provided on both end portions of the roller-body section 22 in the CD direction. During the steady operation of the cutter apparatus 10, the bearers 25 are pressed against the outer circumferential surface 40s of the anvil roller 40. The radius of the circumferential surface of the bearer 25 (the surface pressed against the anvil roller 40) is set, for example, to a value equal to the turning radius of the edge of the cutter blade 21, or a value smaller than the turning radius by a value of the amount of deflection or deformation of the cutter blade 21 caused by the cutting load applied at the time of cutting. Note that the value is not limited to these values, as long as the bearers 25 can be pressed against the outer circumferential surface 40s of the anvil roller 40 without impairing the cutting performance of the cutter blade 21. For example, the radius of the circumferential surface of the bearer 25 may be larger than the turning radius of the cutter blade 21.

Similarly, the anvil roller 40 includes: a roller-body section 42 that is the main body of the roller, and small-diameter sections 43 that are formed coaxially and project at both ends of the roller-body section 42 in the CD direction. The above-described bearing members 14 are respectively arranged on the small-diameter sections 43. The roller-body section 42 is in the form of a flat roller and the outer circumferential surface 40s of the roller-body section 42 is flat throughout the CD direction. That is to say, in this example, the radius of the roller-body section 42 is constant substantially throughout the entire length in the CD direction. Note that the roller profile (outline) of the outer circumferential surface 40s of the roller-body section 42 may not be flat, as long as the cutting performance of the cutter blade 21 or the pressing performance against the bearers 25 is not impaired.

Moreover, a plurality of air vents 45 are formed in a predetermined area A45 of the outer circumferential surface 40s of the roller-body section 42. The air vents 45 functions as part of the collection mechanism 70 that collects punched-out pieces punched from the semi-finished product 1a. This will be described later in a discussion on the collection mechanism 70.

The cutter roller 20 and the anvil roller 40 described above are pressed against each other on the roller-body sections 22 and 42 by a pressing mechanism such as hydraulic cylinders 17 and 17. This will be described in detail with reference to FIGS. 1A and 1B. The cutter apparatus 10 has a housing member 15 for supporting the cutter roller 20 and the anvil roller 40. The housing member 15 has a pair of substantially rectangular frame members 15a and 15a that are respectively provided upright at both sides in the CD direction. Inside each frame member 15a, the small-diameter section 23 of the cutter roller 20 and the small-diameter section 43 of the anvil roller 40 are arranged vertically such that these small-diameter sections are respectively fitted to the bearing members 12 and 14. Furthermore, the hydraulic cylinders 17 and 17 are respectively disposed between the bearing members 14 and 14 of the anvil roller 40 and the corresponding frame members 15a and 15a. The anvil roller 40 is supported so as to vertically move by operations of the hydraulic cylinders 17 and 17 through the bearing members 14 and 14. Accordingly, if the oil pressure of hydraulic fluid which makes the hydraulic cylinders 17 and 17 operate is set as appropriate, the cutter roller 20 and the anvil roller 40 receive a reaction force from the frame members 15a and 15a, and are pressed against each other on the roller-body sections 22 and 42 by a pressing force corresponding to the oil pressure. Note that the hydraulic cylinders 17 may be disposed between the bearing members 12 and 12 of the cutter roller 20 and the corresponding frame members 15a and 15a. Note also that, as the pressing mechanism, air cylinders or feed screw mechanisms may be used instead of the hydraulic cylinders 17.

The drive mechanism 60 includes: a motor as a driving source (not shown); a coupling 61, such as a universal joint, which coaxially couples a drive rotational shaft of the motor and an end of the cutter roller 20 such that the rotational drive force of the motor is transmitted to the cutter roller 20; and drive transmission gears 63 which drive and rotate the anvil roller 40 by transmitting the rotational drive force of the cutter roller 20 to the anvil roller 40. The drive transmission gears 63 are respectively provided on an end of the small-diameter section 23 of the cutter roller 20 and an end of the small-diameter section 43 of the anvil roller 40. When these gears 63 engage with each other, the rotational drive force is transmitted to the anvil roller 40.

Here, the gear ratio (rotation ratio) is 1:1, and thus, the cutter roller 20 and the anvil roller 40 rotate so as to have the same number of rotations. Also, the turning radius of the cutter blade 21 of the cutter roller 20 and the radius of the roller-body section 42 of the anvil roller 40 are set to be equal to each other.

Figure 4:
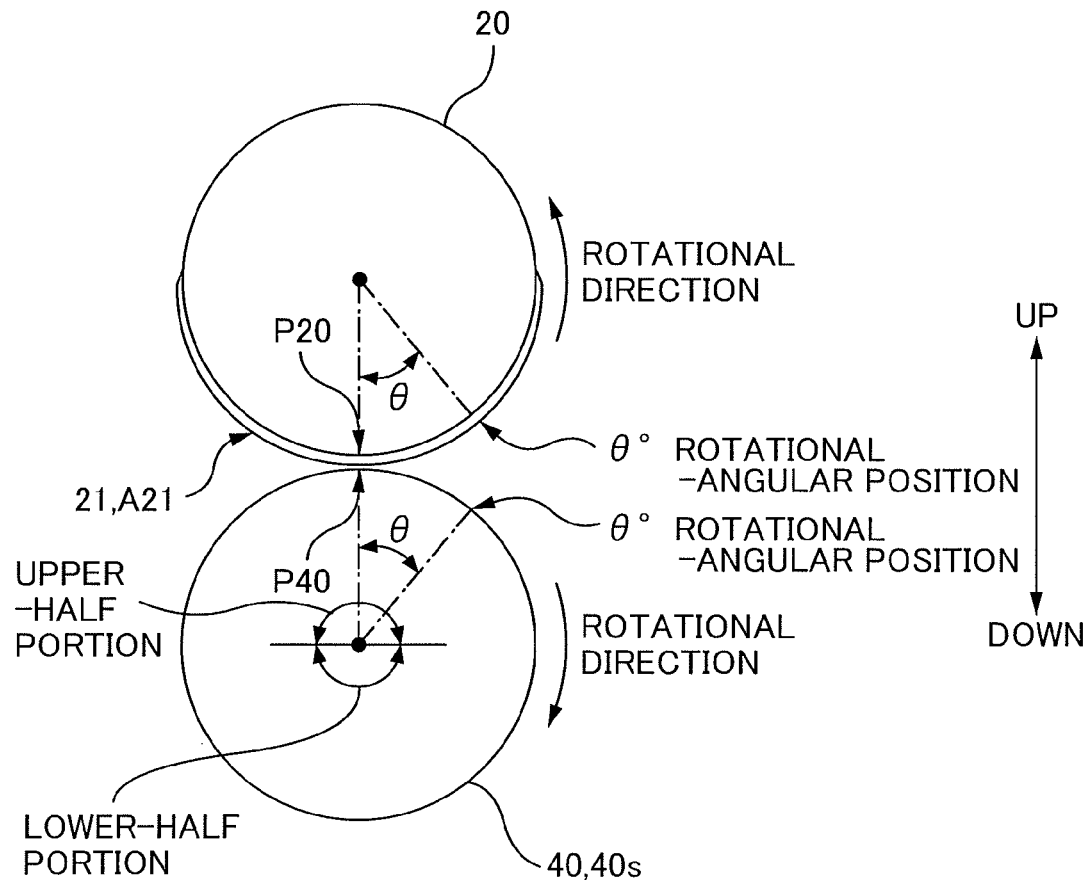
FIG. 4 is an explanatory diagram of a rotational-angular position of the cutter roller 20 and a rotational-angular position of the anvil roller 40.

Accordingly, as shown in FIG. 4, once the gears 63 are engaged with each other such that the cutter roller 20 and the anvil roller 40 are pressed against each other at respective reference positions P20 and P40 in the circumferential direction (rotational direction), then correspondence is established so that the rollers 20 and 40 are always pressed against each other at the same positions in the circumferential direction. For example, as shown in FIG. 4, assume that a position downstream in the rotational direction from the predetermined reference position P20 of the cutter roller 20 at a degree of θ is defined as the θ° rotational-angular position of the cutter roller 20, and that a position downstream in the rotational direction from the predetermined reference position P40 of the anvil roller 40 at a degree of θ is defined as the θ° rotational-angular position of the anvil roller 40. Then, the cutter roller 20 is pressed against the anvil roller 40 at their respective 45° rotational-angular positions, and the cutter roller 20 is pressed against the anvil roller 40 at their respective 90° rotational-angular positions. This relationship holds for any of 0° to 360° rotational-angular positions. This correspondence of the contact positions is maintained, as long as the engagement between the drive transmission gears 63 is not canceled. This is also related to the collection mechanism 70 to be described later. As an example of the reference positions P20 and P40, the following positions shown in FIG. 4 may be used: the position on the center line of the cutter blade-defining area A21 and the corresponding position on the outer circumferential surface 40s of the anvil roller 40. However, other positions may also be used.

FIGS. 5A to 5C are diagrams showing the collection mechanism 70. FIG. 5A is a front view of the anvil roller 40, FIG. 5B is a center longitudinal sectional view of the anvil roller 40 (a cross-sectional view taken along line B-B in FIG. 5C), and FIG. 5C is a view along arrows C-C in FIG. 5A.

The collection mechanism 70 includes a plurality of air vents 45, 45, . . . formed on the outer circumferential surface 40s of the roller-body section 42 of the anvil roller 40. The air vents 45, 45, . . . are configured as follows: sucking air to separate from the semi-finished product punched-out pieces which are punched from the semi-finished product 1a by the cutter blade 21 of the cutter roller 20 1a; holding the pieces on the outer circumferential surface 40s of the anvil roller 40; and removing the pieces from the outer circumferential surface 40s by discharging air at proper timing after the separation.

More specifically, as shown in FIG. 5B, the air vents 45, 45, . . . communicate with air flow paths 47, 47, . . . formed inside the anvil roller 40 in the CD direction, and the air flow paths 47, 47, . . . reach one end face 42a of the roller-body section 42 of the anvil roller 40. An air suction/discharge drum 72 is placed near this end face 42a; the drum 72 supplies air to the air flow paths 47, 47, . . . and sucks air from the air flow paths 47, 47, . . . , depending on the position of the anvil roller 40 in the rotational direction. For example, the air suction/discharge drum 72 sucks air from the air flow path 47 through the range of the upper-half portion that faces the cutter roller 20 in the rotational direction of the anvil roller 40 as shown in FIG. 4. On the other hand, the air suction/discharge drum 72 supplies air into the air flow path 47 through the range of the lower-half portion that does not face the cutter roller 20. Thus, while moving through the upper-half range, the air vents 45 of the anvil roller 40 suck air; thereby punched-out pieces punched from the semi-finished product 1a are separated from the semi-finished product 1a and are held on the outer circumferential surface 40s. Thereafter, while moving through the lower-half range, the air vents 45 discharge air to the punched-out pieces; thereby the pieces held on the outer circumferential surface 40s are removed from the outer circumferential surface 40s and drop into an appropriate collection box (not shown).

The air vents 45, 45, . . . are arranged corresponding to the shape of the leg openings 1h, which is the shape to be punched, on the outer circumferential surface 40s of the anvil roller 40 as shown in FIG. 5A. Thus, the air-vent arrangement area A45 (see the area surrounded by the dotted lines) is formed in substantially the center in the CD direction on the outer circumferential surface 40s. In the circumferential direction of the anvil roller 40, the air-vent arrangement area A45 exists only within a region approximately one half of the circumference, but the area A45 does not exist within the remaining region approximately one half of the circumference. This is because, as shown in FIG. 2, the leg openings 1h of the semi-finished product 1a occupy an area approximately half of a single product in the MD direction.

The correspondence between the air-vent arrangement area A45 and the rotational-angular position of the cutter blade-defining area A21 of the cutter roller 20 is established by the engagement between the drive transmission gears 63. Thus, when the air-vent arrangement area A45 passes the contact position, it always faces the cutter blade-defining area A21 of the cutter roller 20, which results in ensuring that the punched-out pieces punched by the cutter blade 21 are held on the air-vent arrangement area A45.

<<<Dynamic Balance Correction of Cutter Roll 20 and Anvil Roll 40>>>

It is necessary that the dynamic balance of the cutter roller 20 and the anvil roller 40 is corrected from the standpoint of the extension of the life of the cutter blade 21. In other words, it is necessary to place the center of gravity of each roller 20 (40) as close as possible to its own rotational axis C20 (C40) so as to coincide with the rotational axis. The reason is as follows: if the center of gravity is located far away from the rotational axis C20 (C40), the roller 20 (40) vibrates during rotation, whereby the cutter blade 21 hits the outer circumferential surface 40s of the anvil roller 40 locally and heavily, which causes breakage, wear, etc of the cutter blade 21 and shorten the life thereof.

Incidentally, displacement of the center of gravity in the cutter apparatus 10 of this embodiment is caused by the following reasons: for the cutter roller 20, the cutter blade 21 is placed asymmetrically with respect to the rotational axis C20; and for the anvil roller 40, the air vents 45 and the air flow paths 47 described above are formed asymmetrically with respect to the rotational axis C40.

As an indicator of the dynamic balance, the "balance quality" is defined in JIS B 0905; in this embodiment, the concept of the "balance quality" is referred. In this embodiment, the dynamic balance of the roller 20 or 40 is corrected as required so that the sum of the values of the balance quality of the roller at one end and at the other end in the CD direction is 6 or less for both the cutter roller 20 and the anvil roller 40.

By the above correction, the rotational vibration of the cutter roller 20 and the anvil roller 40 is suppressed or reduced, which permits the life of the cutter blade 21 to extend to substantially the longest level. The reason why the life can extend to substantially the longest level when the above sum is 6 or less will be described later.

The method of calculating the balance quality will be described hereinafter. According to JIS B 0905, the balance quality is defined by Equation 1 below.

$$\text{Balance quality (mm/sec)} = e \times \omega \quad (1)$$
$$= e \times 2\pi \times n/60$$
$$= e \times n/9.55$$

In the above equation, $\omega$ is the angular speed (rad/sec) of rotation, n is the rotational speed (min$^{-1}$) of the roller, and e is the specific unbalance (mass eccentricity distance) (mm).

The rotational speed n of the roller is the maximum rotational speed of the roller at the time when the semi-finished product 1a is punched by the cutter roller 20 and the anvil roller 40, i.e., the maximum rotational speed during the steady operation (during production).

The specific unbalance e is expressed by Equation 2 below using the unbalance U (kg·m) and the roller mass M (kg).

$$\text{Specific unbalance } e \text{ (mm}^{-1}\text{)} = U/M \quad (2)$$

Further, the unbalance U is expressed by Equation 3 below.

$$\text{Unbalance } U \text{ (kg·m)} = \text{residual unbalance amount (kg)} \times \text{balance correction radius (mm)} \quad (3)$$

By sequentially substituting Equation 2 and Equation 3 into Equation 1, the balance quality is expressed as Equation 4 below.

$$\text{Balance quality (mm/sec)} = (U/M) \times n/9.55 \quad (4)$$
$$= \text{residual unbalance amount} \times$$
$$\text{balance correction radius}/M \times n/9.55$$

The residual unbalance amount (kg) is acquired by measurement for one end and the other end of the roller in the CD direction using a two-plane balancing machine which is defined in JIS B 7737. The method of measuring the residual unbalance amount, etc. using the two-plane balancing machine will be described later.

As the value of the balance correction radius, the turning radius of the cutter edge of the cutter blade 21 is set for the cutter roller 20, and the radius of the roller-body section 42 is set for the anvil roller 40. The reason for this is that it is on the roller surface that rotational vibration causes a problem. That is to say, the blade edge of the cutter roller 20 and the roller-body section 42 of the anvil roller 40 come into contact with the semi-finished product 1a that passes the nip between the rollers 20 and 40, and they cut the product. Therefore, calculation using the turning radius of the blade edge of the cutter roller 20 and the radius of the roller-body section 42 of the anvil roller 40 makes it possible to detect the vibration at the time of cutting of the semi-finished product 1a by the rollers 20 and 40.

By substituting the measured residual unbalance amount and the balance correction radius into Equation 4, the balance quality of the roller for which the calculation is performed can be determined for each of one end and the other end of the roller in the CD direction. The sum of the values of the balance quality at the one end and at the other end is calculated as the above-described sum as the indicator of the dynamic balance according to this embodiment.

For example, a specific example of the calculation will be described using the case of the anvil roller 40 before dynamic balance correction in Table 1 (see FIG. 9) described later. The following values required for the calculation are shown in Table 1: the residual unbalance amounts and the balance correction radii at one end (L side) and at the other end (R side); the roller mass; and the roller rotational speed. By substituting these values into Equation 4, the balance qualities at the one end and at the other end of the anvil roller 40 in Table 1 are calculated as follows.

$$\text{Balance quality at one end (mm/sec)} = 1.203 \times 95/300 \times 200/9.55$$
$$= 7.98 \text{ (mm/sec)}$$
$$\text{Balance quality at the other end (mm/sec)} = 0.605 \times 95/300 \times 200/9.55$$
$$= 4.01 \text{ (mm/sec)}$$

From the above, the sum of the values of the balance quality at one end and at the other end is 11.99 (=7.98+4.01).

Then, the dynamic balance correction is performed for the roller in which the value of the above-described sum exceeds 6, so that the value of the sum becomes 6 or less for both rollers 20 and 40. In this way, the cutter apparatus 10 of this embodiment in which the life of the cutter blade 21 has extended is achieved.

Figure 6A:
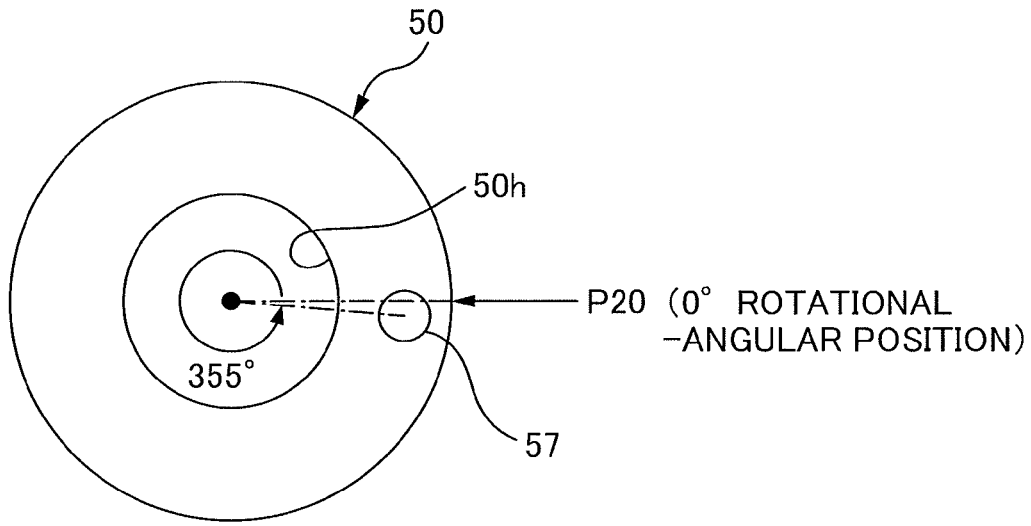
FIG. 6A is a view along arrows VIa-VIa in FIG. 3A.
Figure 6B:
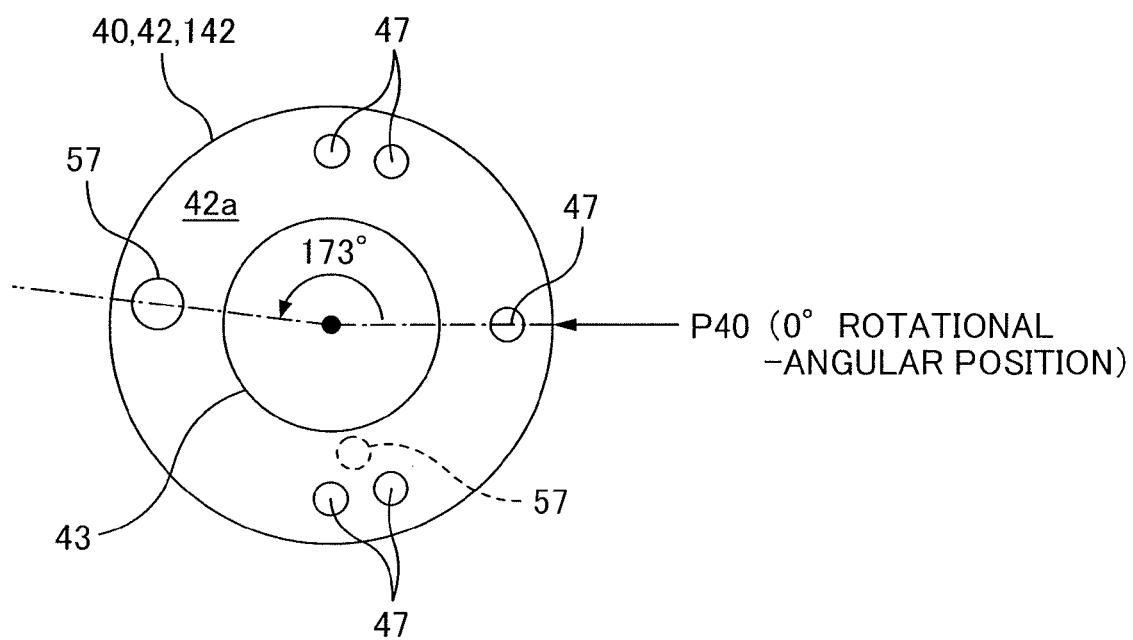
FIG. 6B is a view along arrows VIb-VIb in FIG. 3B.

The dynamic balance correction is performed in the following manner. FIG. 6A is a view along arrows VIa-VIa in FIG. 3A, shown as an explanatory diagram of the correction. FIG. 6B is a view along arrows VIb-VIb in FIG. 3B. Note that, although the description will be made taking the case that the roller to be corrected is the cutter roller 20 as an example, a similar result will also be obtained when it is the anvil roller 40.

First, when the roller 20 will be corrected, balance weights 50 and 50 are respectively placed on both end faces 22a and 22a of the roller-body section 22 of the roller 20 in the CD direction, as shown in FIG. 3A. Specifically, as shown in FIG. 6A, the balance weight 50 is a metal disc having a perfect circular shape, for example. At the center of the flat surface thereof, a through hole 50h is formed concentric with the center C50 of the circle. Therefore, as shown in FIG. 3A, the small-diameter sections 23 of the roller 20 are respectively fitted into the through holes 50h, and the balance weights 50 abut against the end faces 22a of the roller-body section 22. Under this condition, the balance weights 50 are bolted to the small-diameter sections 23, whereby the balance weights 50 are integrally secured to the roller 20.

Thereafter, as shown in FIG. 6A, based on the residual unbalance amount at one end in the CD direction, a hole 57 (corresponding to a dynamic-balance correction section) is formed by drilling the balance weight 50 at the one end, whereby the dynamic balance is corrected. That is, the hole 57 is formed in a portion of the balance weight 50 corresponding to a rotational-angular position at which the residual unbalance amount has been detected (hereinafter also referred to as an unbalance position). Thereby, the mass at that rotational-angular position is selectively removed, which results in correction of the dynamic balance at the one end in the CD direction. For example, in the case of Table 1 in FIG. 9, the residual unbalance amount on the left side, which corresponds to the one end side, is located at a 355° rotational-angular position. Therefore, the hole 57 is formed in a portion at the 355° rotational-angular position of the balance weight 50.

Also, as for the other end (on the right side) in the CD direction, the dynamic balance is corrected in a similar way by forming the hole 57 in the balance weight 50 at the other end (on the right side) based on the residual unbalance amount and the unbalance position at the other end (on the right side).

Incidentally, as described earlier with reference to FIG. 4, the rotational-angular position related to the unbalance position described above is a position indicated by an angular coordinate of 0° to 360° which are sequentially assigned along the rotational direction of the roller 20 (40) from the predetermined reference position P20 (P40) of the roller 20 (40) as the start point. Also, as already described, when the rotational direction of the cutter roller 20 is counterclockwise, for example, the rotational direction of the anvil roller 40 is clockwise. That is, the rotational directions are opposite to each other. Furthermore, as also described earlier, during the steady operation, the cutter roller 20 and the anvil roller 40 which are rotating are always pressed against each other at their corresponding rotational-angular positions, such as at the reference positions P20 and P40.

Thereafter, the roller 20 is placed in the two-plane balancing machine to measure again the balance quality of the roller 20 for both the right and left sides in the CD direction. If the sum of the measured values of the balance quality is 6 or less, the correction is terminated. If the sum exceeds 6, the dynamic balance correction described above is performed again, and this operation is repeated until the sum of the values of the balance quality becomes 6 or less.

The dynamic balance correction operation as described above is performed for at least one of the cutter roller 20 and the anvil roller 40 as required. When the sum of the values of the balance quality becomes 6 or less for both rollers 20 and 40, then the cutter apparatus 10 of this embodiment is achieved.

In other words, both the cutter roller 20 and the anvil roller 40 are not necessarily the rollers subjected to the dynamic balance correction, and it is sufficient to perform the correction for only either one of them. For example, if one of the rollers meets the requirement that the sum of the values of the balance quality is 6 or less without dynamic balance correction, the dynamic balance may be corrected by forming the dynamic-balance correction section 57 for only the other roller that does not meets the requirement.

Depending on the structure of the rollers, the balance weights 50 may not be used. In this case, the dynamic balance may be corrected by directly drilling the end faces 22a (42a) of the roller-body section 22 (42). FIGS. 7A and 7B are explanatory diagrams of this correction; FIG. 7A is a front view of the cutter roller 20 and FIG. 7B is a front view of the anvil roller 40.

For example, assuming that the roller 20 (40) includes: a shaft 122 (142) that is a cylindrical core section including the rotational axis C20 (C40) inside; and a surface-layer section 124 (144) formed integrally covering the outer circumferential surface of the shaft 122 (142) substantially uniformly. In this case, if the shaft 122 (142) is made of a material having lower hardness than the surface-layer section 124 (144), the dynamic balance may be corrected by forming the holes 57 (corresponding to the dynamic-balance correction sections) by drilling directly on the faces of the shaft 122 (142) exposed at the end faces 22a (42a) of the roller-body section 22 (42). With such a roller structure, it is unnecessary to drill the hard surface-layer section 124 (144). This makes the correction operation easy.

The reason that the surface-layer section 124 (144) has high hardness is that the durability of the cutter blade 21 of the cutter roller 20 increases and that the anvil roller 40 receives the cutter blade 21 on the outer circumferential surface 40s.

The roller structure will be describe in more detail below. In the case of this embodiment, the cutter roller 20 is configured as follows. A cylindrical body made of SCM 440 is used as its shaft 122. Onto the middle portion of the shaft 122 in the CD direction, fitted is a sleeve 124a made of a hard metal having the cutter blade 21, as the surface-layer section 124. Onto both sides of the middle portion, fitted are sleeves 124b made of SKD 11. Moreover, onto the outer sides of the sleeves 124b, fitted are ring members 124c made of a hard metal as the surface-layer section 124, the ring members 124c serving as the bearers 25. Similarly, the anvil roller 40 is configured as follows. A cylindrical body made of SCM 440 is used as its shaft 142. Onto the middle portion of the shaft 142 in the CD direction, fitted is a sleeve 144a made of a hard metal as the surface-layer section 144, the sleeve 144a serving as a blade receiver. Onto both sides of the middle portion, fitted are sleeves 144b made of SKD 11. Moreover, onto the outer sides of the sleeves 144b, fitted are ring members 144c made of a hard metal as the surface-layer section 144, the ring members 144c serving as portions receiving the bearers 25.

Accordingly, as for both of the cutter roller 20 and the anvil roller 40, the shaft 122 (142) made of SCM 440 having lower hardness than hard metal is exposed on the end faces 22a (42a) of the roller-body section 22 (42). This makes it comparatively easier to form the holes 57 by drilling the end faces 22a (42a), the holes 57 serving as the dynamic-balance correction sections.

Regarding the fitting described above, it is basically advisable to secure all of the sleeves 124a and 124b (144a and 144b) and the ring members 124c (144c) to the shaft 122 (142) by tight fitting. However, the sleeve 124b (144b) made of SKD 11 may be secured to the shaft 122 (142) by loose fitting or transition fitting and then screw fastening.

Also, if using the above method of forming the holes 57 by directly drilling the end faces 22a (42a) of the roller-body section 22 (42), the dynamic balance correction becomes markedly easy for the anvil roller 40 in particular. The reason is as follows. As described earlier with reference to FIGS. 5A and 5B, in the case of the anvil roller 40, the air suction/discharge drum 72 is opposed to one end face 42a of the roller-body section 42. Therefore, if the balance weight 50 is placed to abut against the one end face 42a of the roller-body section 42, the balance weight 50 will interfere with the air suction/discharge drum 72, which will require modification of the air suction/discharge drum 72. For this reason, in the case of the anvil roller 40, especially, it is advantageous to use the method of forming the holes 57 directly at the end faces 42a of the roller-body section 42 as described above. In the cutter apparatus 10 of this embodiment, as shown in FIGS. 3B and 6B, the dynamic balance correction on the left side of the anvil roller 40 in the CD direction is performed by this method. That is, the hole 57 is formed directly at the end face 42a of the roller-body section 42 and used as the dynamic-balance correction sections 57. However, depending on the unbalance position, it is possible that the dynamic-balance correction section 57 interferes with the position of any air flow path 47 at the time of forming the section 57 in the end face 42a. In such a case, as shown by the dotted line in FIG. 6B, the dynamic-balance correction section 57 may be formed at an inner position on the end face 42a in the radial direction with respect to the position of the air flow path 47.

With the above configuration of FIG. 3B, in which the balance weight 50 is placed on only the right side in the CD direction, the weight balance between the left and right sides is worsened. However, the influence of the weight balance on the rotational vibration is comparatively small, causing no large problem.

Naturally, in some cases, the balance weight 50 may be used for the anvil roller 40. In such cases, a modified balance weight will be provided, which has through holes communicating with the air flow paths 47, 47, . . . at positions corresponding to the air flow paths 47, 47, . . . of the roller-body section 42 of the balance weight 50 and does not interfere with the air suction/discharge drum 72.

In the two-plane balancing machine described above, along with measurement of the residual unbalance amounts, the rotational-angular positions at which the residual unbalance amounts are present, i.e., the unbalance positions are also measured (e.g., see Tables 1 to 3 in FIG. 9). It is desirable that the unbalance positions after the dynamic balance correction will have a positional relationship as follows.

Assuming that, of the cutter roller 20 and the anvil roller 40, one roller 20 (40) is a first roller and the other roller 40 (20) is a second roller. As for the first roller 20 (40), both the unbalance position related to the residual unbalance amount on the one-end side in the CD direction and the unbalance position related to the residual unbalance amount on the other-end side fall within the range of the 90° to 270° rotational-angular positions; and as for the second roller 40 (20), both the unbalance position related to the residual unbalance amount on the one-end side in the CD direction and the unbalance position related to the residual unbalance amount on the other-end side fall within the range of the 270° to 360° or 0° to 90° rotational-angular positions.

Having such a positional relationship, the directions of the centrifugal forces caused by the residual unbalance amounts of the rollers 20 and 40 can be substantially the same. Thus, the influences of the rotational vibrations of the rollers 20 and 40 on the cutting loads are cancelled.

Figure 8:
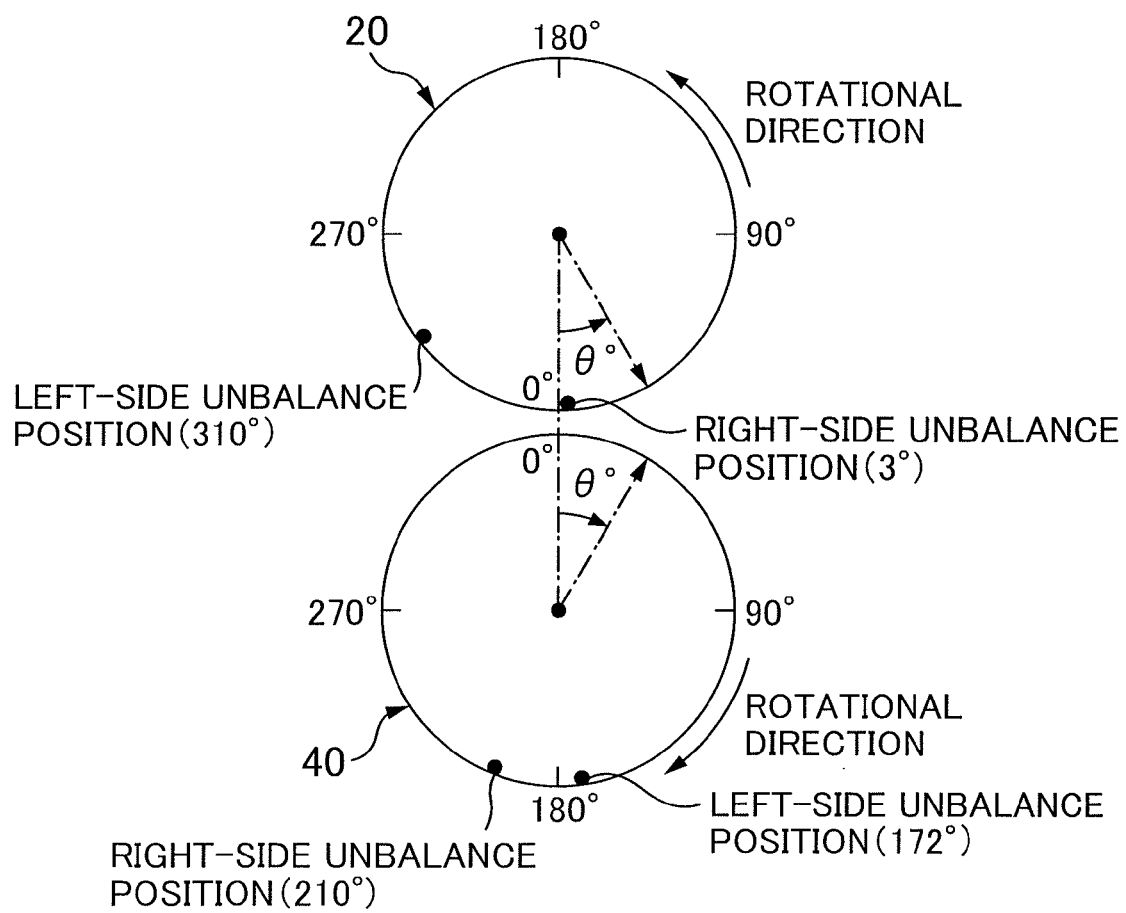
FIG. 8 is an explanatory diagram of a desirable positional relationship of residual unbalances between the cutter roller 20 and the anvil roller 40 related to Table 3.

For example, in the case of Table 3 in FIG. 9, the positions of the residual unbalances of the rollers 20 and 40 have a positional relationship shown in FIG. 8, which satisfies the positional relationship described above. Under such a positional relationship, when the direction of the centrifugal force by the residual unbalance amounts of the cutter roller 20 is downward, the direction of the centrifugal force by the residual unbalance amounts of the anvil roller 40 is also substantially downward. Similarly, when the direction of the centrifugal force by the residual unbalance amounts of the cutter roller 20 is upward, the direction of the centrifugal force by the residual unbalance amounts of the anvil roller 40 is also substantially upward. This makes it easy to keep the distance between the cutter roller 20 and the anvil roller 40 substantially constant. Therefore, a phenomenon such as periodic strong bumps of the rollers at a given rotational-angular position becomes less likely to occur. Thus, the cutting load can be uniform over the entire circumference of the cutter roller 20. As a result, local wear, etc. on the cutter blade 21 and the outer circumferential surface 40s of the anvil roller 40 is effectively suppressed or reduced, and thus extension of the life of the cutter blade 21, etc. can be achieved. Also, a cut error becomes less likely to occur.

<<<Relationship Between Sum of Balance Quality and Life of Cutter Blade 21>>>

The relationship between the sum of the values of the balance quality and the life of the cutter blade 21 will be described hereinafter. Experiments were performed to examine the relationship.

First, the experiment method will be described. Experiment standards are shown in Tables 1 to 3 in FIG. 9, where the sums of the values of the balance quality are examined among the three standards.

Table 1 shows the specifications of the rollers 20 and 40 in the first standard. In the first standard, no dynamic balance correction was performed. The sums of the values of the balance quality of these rollers 20 and 40 were measured, and the results were 1.68 for the cutter roller 20 and 11.99 for the anvil roller 40, as shown in the right portion of Table 1.

Table 2 shows the specifications of the rollers 20 and 40 in the second standard. In the second standard, the dynamic balance correction was performed only for the anvil roller 40 of the rollers 20 and 40 in the first standard. The sum of the values of the balance quality of the anvil roller 40 after the dynamic balance correction was 6.13 as shown in the right portion of Table 2.

Table 3 shows the specifications of the rollers 20 and 40 in the third standard. In the third standard, the dynamic balance correction was further performed for both the rollers 20 and 40 in the second standard. The sums of the values of the balance quality after the dynamic balance correction were measured, and the results were 0.04 for the cutter roller 20 and 1.12 for the anvil roller 40, as shown in the right portion of Table 3.

These experiment standards can be considered as follows: while the sum of the values of the balance quality of the cutter roller 20 was substantially kept at a fixed value (1.68, 1.68, and 0.04) in the level causing no problem of rotational vibration, the sum of the values of the balance quality of the anvil roller 40 were significantly different among the three standards (11.99, 6.13, and 1.12). In other words, in these experiment standards, by changing only the sum of the values of the balance quality of one roller 40, the influence of the sum on the life of the roller is made assessable.

Meanwhile, the life of the cutter blade 21 was assessed in the following manner. The rollers 20 and 40 in each experiment standard were mounted in the cutter apparatus 10, and the cutter apparatus 10 actually punched out the leg openings 1h from the semi-finished product 1a continuously. The assessment was made based on the cumulative number of times of cutting at the time point when cut errors had occurred continuously in two or more product pieces.

However, in the above assessment, the oil pressure value of the hydraulic cylinders 17 at the start of the experiment was set at a set value used during the steady operation. Every time when a cut error occurred, the oil pressure value raised to a level at which no cut error occurred any more. After the final rise of the oil pressure value to its upper limit value, when cut errors had occurred continuously in two or more product pieces, the cumulative number of times of cutting at that time point was determined as the cumulative number of times of cutting to be assessed, i.e., the life of the cutter blade. As the semi-finished product 1a, used was one which is formed by stacking two pieces of nonwoven fabric and bonding them together, the nonwoven fabric being made of polypropylene fiber having a basis weight of 20 to 50 (g/m$^2$).

Figure 10:
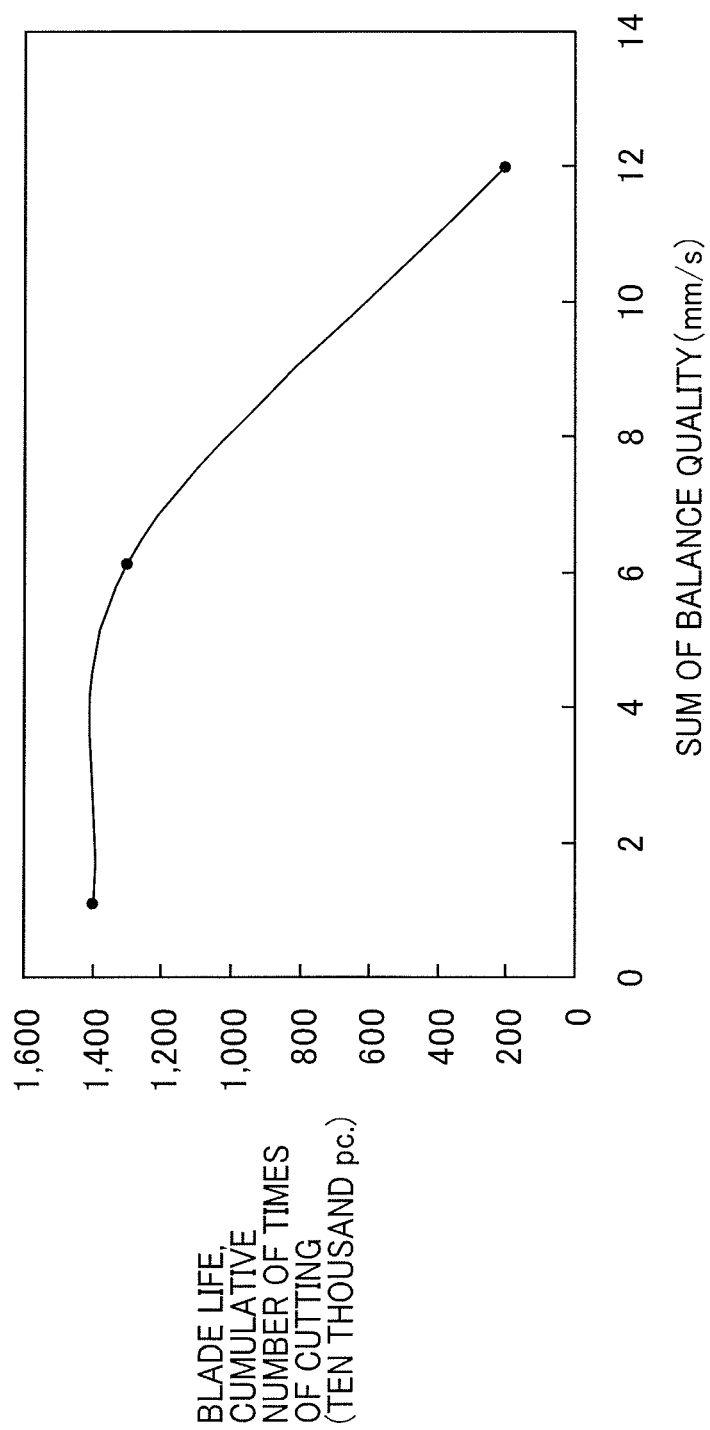
FIG. 10 is a graph showing the experiment results.

FIG. 10 shows a graph of the experiment results, where the horizontal axis represents the sum of the values of the balance quality and the vertical axis represents the cumulative number of times of cutting. Note that the sum of the values of the balance quality of the anvil roller 40 was used as the values of the sum of balance quality plotted on the graph for the reason described above.

From the graph of FIG. 10, it is found that smaller sum of the values of the balance quality leads to longer life of the cutter blade 21. It is also found that the life is substantially constant near the value of the sum of "6," that is, the effect of life extension has been maximized in the range of 6 or less. Therefore, it is considered that the life can be extended to the maximum level by correcting the dynamic balance so that the sum of the values of the balance quality becomes 6 or less.

In comparison between Table 2 and Table 3 in FIG. 9, the balance qualities of the cutter roller 20 are different: one is 1.68 and the other is 0.04. Despite of this difference, the life of the cutter blade 21 little changed, i.e., changed merely from 13 million pieces to 14 million pieces; the life has been substantially maximized. In other words, the influence of the difference between 1.68 and 0.04 on the life is considered to be small.

Accordingly, without any problem, it can be considered that the graph of FIG. 10 is the experiment results obtained by varying only the condition of the balance quality of the anvil roller 40 among three standards of 11.99, 6.13, and 1.12 while substantially fixing the condition of the balance quality of the cutter roller 20 to 1.68 where the influence of the balance quality is small (or suppressing the balance quality to 1.68 or less where the influence thereof is small). Moreover, since the influence of the rotational vibration on the life is considered to be equivalent between the cutter roller 20 and the anvil roller 40, the tendency described above is considered to also apply to the cutter roller 20. Therefore, it is considered appropriate to evaluate the influence of the sum of the values of the balance quality on the life of the cutter blade 21 for each roller based on this graph.

<<<Measurement Methods for Residual Unbalance Amount and Unbalance Position>>>

The methods for measuring the residual unbalance amount and the unbalance position by a two-plane balancing machine will be described hereinafter.

For the above measurements, a two-plane balancing machine defined in JIS B 7737 is used. An example of such a machine is a force detection type dynamic balancing machine (Model: GH-528C-C1) from Akashi Corporation (Mitutoyo Corporation). This machine is of a so-called flexible type, where the roller to be measured is rotating while being supported by soft support bearings, whereby vertical vibration of the rotating roller is measured and then converted to the residual unbalance amount, etc.

Figure 11:
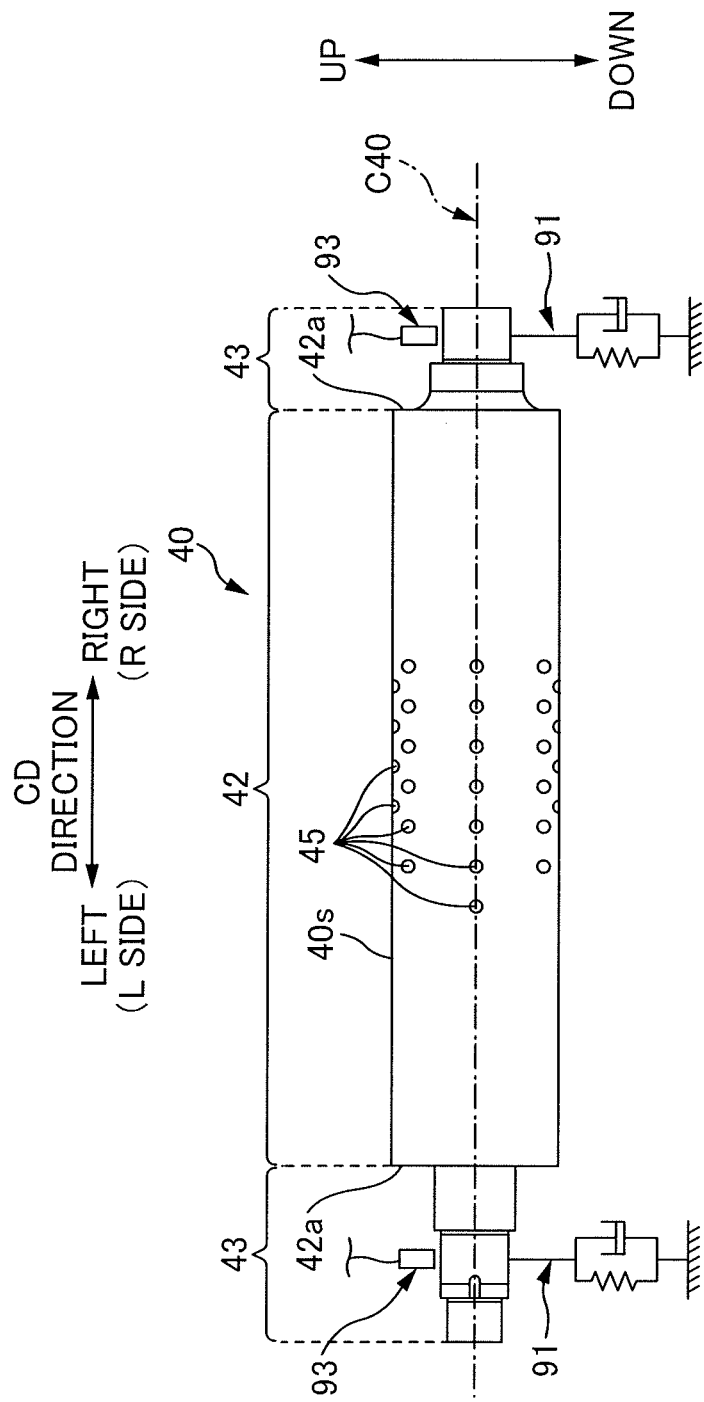
FIG. 11 is an explanatory diagram of a two-plane balancing machine.

More specifically, first, the balance correction radius is input into the machine. Thereafter, as shown in the front view of FIG. 11, the roller 40 to be measured is rotatably supported by the foregoing soft support bearings 91 on the small-diameter sections 43 (sections supported by the bearing members 14) at both ends of the roller. Then, the roller 40 is rotated about the rotational axis C40 at the foregoing rotational speed n by a motor (not shown) attached to the machine; the roller 40 generates vertical vibrations due to unbalance. The vertical vibrations are detected by vibrometers 93 placed on the outer circumferential surfaces of the small-diameter sections 43. The detected vertical vibrations are computed by a computer (not shown) and then are converted to a vertical vibration at the position of the L-side end face 42a and a vertical vibration at the position of the R-side end face 22a. The computer computes the data of these vertical vibrations and obtains the residual unbalance amounts and the unbalance positions on both the L side and the R side, the unbalance positions being the phases (rotational-angular positions) of the residual unbalance amounts. The result is displayed on a display, etc. of the machine. Such measurements are performed, not only for the anvil roller 40, but also for the cutter roller 20, to acquire the values of the residual unbalance amounts and the unbalance positions in Tables 1 to 3 described above.

The computation for determining the residual unbalance amounts and the unbalance positions from the data of the vertical vibrations at positions on the end faces 42a of the roller-body section 42 is too complicated to explain. Therefore, the principle of the computation will be described hereinafter. It goes without saying that the above computer performs the operation described hereinafter by mathematical computations.

First, from the measured data of the vertical vibration at a position on each of the end faces 42a of the roller-body section 42, obtained are the amplitude at the position on the end face 42a and the phase of the amplitude. The definition of "phase" is the same as the rotational-angular position described above. By using a so-called influence coefficient method, the condition of a correction weight for balancing the roller 40 can be determined from the amplitude and the phase.

Here, the correction weight and the residual unbalance amount are in a positional relationship having point-symmetry with respect to the rotational axis C40 of the roller 40. Therefore, once the correction weight is determined, the residual unbalance amount, etc. can also be determined.

How to determine the correction weight using the influence coefficient method is described in detail in Non-Patent Document, Osami Matsushita, Masato Tanaka, Hiroshi Kanki, and Masao Kobayashi, "Vibration of Rotating Machinery—Fundamentals of Practical Vibration Analysis," Corona Publishing Co., Ltd., 1st ed., Oct. 2, 2009, pp. 103-135, especially in "5.8 Solution of Two-Plane Balance," pp. 131-133.

Accordingly, how to determine the residual unbalance amount, etc. will be described hereinafter through description on how to determine the correction weight by appropriately referring to the contents of the above document.

Figure 12:
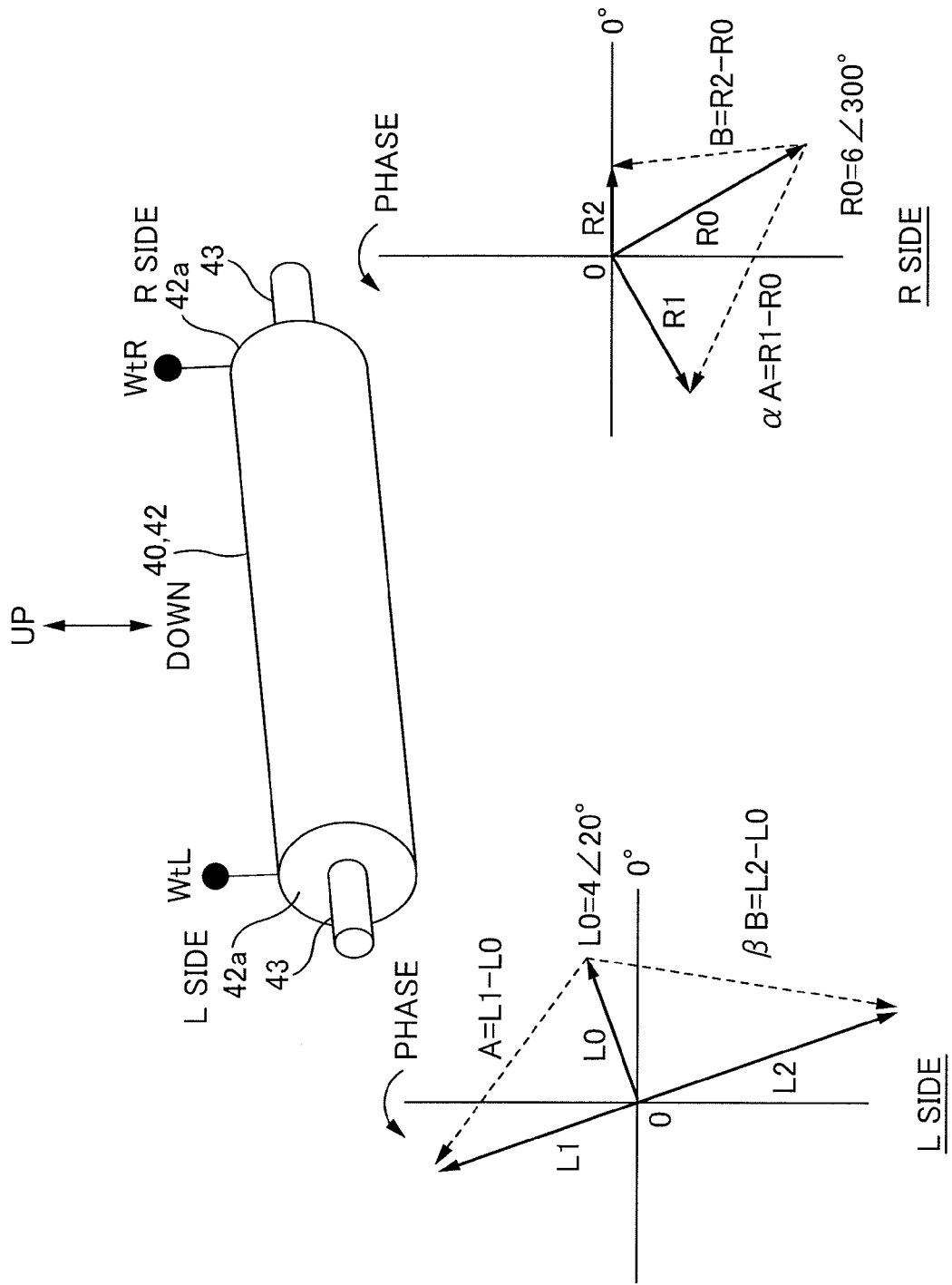
FIG. 12 is an explanatory diagram showing how to calculate correction weights $W_{cL}$ and $W_{cR}$.

Two-plane balancing of the roller 40 as shown in FIG. 12 on the L side and the R side thereof is performed as follows. First, the roller 40 is rotated, and vertical vibrations are measured on L-side and R-side correction planes 42a (planes 42a for balancing; corresponding to the end faces 42a of the roller-body section 42 described above). The measured data of these vertical vibrations are acquired as initial vibration L0 and initial vibration R0, respectively. Next, a known test weight $W_{tL}$ is placed on only the L-side correction plane 42a. In this state, the roller 40 is rotated, vertical vibrations are measured on the L side and the R side, and the measured data of these vertical vibrations are acquired as vibration L1 and vibration R1, respectively. Finally, the test weight $W_{tL}$ on the L side is removed, and a known test weight $W_{tR}$ is placed on only the R-side correction plane 42a. In this state, the roller 40 is rotated, vertical vibrations are measured on the L side and the R side, and the measured data of these vertical vibrations are acquired as vibration L2 and vibration R2, respectively. The test weights $W_{tL}$ and $W_{tR}$ are placed at positions of the balance correction radius, for example.

Then, complex coefficients α and β between influence coefficients are introduced as shown in Equations 5 and 6 below. Also, graphical calculation as shown in FIG. 12 is used in combination. Note that the following L0, L1, L2, R0, R1, R2, A, B, α, and β are vectors, and addition, subtraction, multiplication, and division thereof are performed as vectors.

$$R1-R0=\alpha(L1-L0)\equiv\alpha A \qquad (5)$$

$$L2-R0=\beta(R2-R0)\equiv\beta B \qquad (6)$$

Meanwhile, correction weights $W_{cL}$ and $W_{cR}$ to be placed on the two right and left correction planes 42a are expressed by their respective ratios θ and φ to the test weights $W_{tL}$ and $W_{tR}$, as follows.

$$W_{cL}=\theta W_{tL} \qquad (7)$$

$$W_{CR}=\phi W_{tR} \qquad (8)$$

The ratios determining the correction weights $W_{tL}$ and $W_{tR}$ should be set so as to generate vibrations opposite in phase to the initial vibrations L0 and R0. Therefore, the ratios are determined from Equation 9 below.

$$-\begin{bmatrix}L0\\R0\end{bmatrix}=\begin{bmatrix}L1-L0 & L2-L0\\R1-R0 & R2-R0\end{bmatrix}\begin{bmatrix}\theta\\\phi\end{bmatrix}\rightarrow-\begin{bmatrix}L0\\R0\end{bmatrix} \qquad (9)$$

$$=\begin{bmatrix}A & \beta B\\\alpha A & B\end{bmatrix}\begin{bmatrix}\theta\\\phi\end{bmatrix}$$

From Equation (9), Equation (10) below is derived.

$$\begin{bmatrix}\theta\\\phi\end{bmatrix}=\frac{1}{1-\alpha\beta}\begin{bmatrix}(\beta R0-L0)/A\\(\alpha L0-R0)/B\end{bmatrix} \qquad (10)$$

Therefore, θ and φ are determined by substituting the measured data of vibrations L0, L1, L2, R0, R1, and R2 into Equation 10 via Equations 5 and 6, and then the resultant θ and φ are substituted into Equations 7 and 8. Thus, the correction weights $W_{cL}$ and $N_{cR}$ can be calculated since the test weights $W_{tL}$ and $W_{tR}$ are known.

The above method will be described below in a specific calculation example. First, assume that the measured data of the vertical variations L0, L1, L2, R0, R1, and R2 shown in Table 4 in FIG. 13 were obtained by the balancing machine described above.

From Table 4, L0=4∠20° and R0=6∠300°, where "4" related to the vector L0 is the scalar amount of the vector L0, and ∠20° is the direction of the vector L0 on polar coordinates in FIG. 12. Note that the vector L0 is herein referred to simply as L0 as described above. This also applies to the other vectors L1, L2, R0, R1, R2, A, B, α, β, and 1.

Also, from the relationship among the vectors in FIG. 12, Equations 11 and 12 below are established. Note that the scalar amounts such as "7" and the angles such as ∠144° related to the following vectors such as A may be calculated using the cosine rule of trigonometric functions, etc. or may be obtained by creating the drawing of FIG. 12 and measuring the values using a protractor, a ruler, etc.

$$L1-L0=A=7\angle 144°  \quad (11)$$

$$R1-R0=\alpha A=7.7\angle 155° \quad (12)$$

From Equations 11 and 12, α is obtained as follows.

$$\alpha=\alpha A/A=1.07/11° \quad (13)$$

Also, from the relationship among the vectors in FIG. 13, Equations 14 and 15 are established.

$$R2-R0=B=5.5\angle 102° \quad (14)$$

$$L2-L0=\beta B=9\angle 265° \quad (15)$$

From Equations 14 and 15, β is obtained as follows.

$$\beta=\beta B/B=1.64\angle 163° \quad (16)$$

Furthermore, based on α, L0, β, and R0, Equations 17, 18, and 19 below are established.

$$\alpha L0=4.28\angle 31°$$

$$\alpha R0=9.84\angle 103°$$

$$\alpha\beta=1.75\angle 174°$$

Accordingly, θ and φ are determined as follows.

$$\theta = \frac{\beta R0 - L0}{(1-\alpha\beta)A} = \frac{10\angle 125°}{(2.75\angle 356°)(7\angle 144°)} = 0.52\angle 345° \quad (20)$$

$$\phi = \frac{\alpha L0 - R0}{(1-\alpha\beta)B} = \frac{7.25\angle 86°}{(2.75\angle 356°)(5.5\angle 102°)} = 0.48\angle 348° \quad (21)$$

Note that the vector "1" in the denominator in Equations 20 and 21 represents "1∠0°."

Based on the above values of θ and φ and Equations 7 and 8, the correction weights $W_{cL}$ and $W_{cR}$ are calculated as follows, with the test weights $W_{tL}$ and $W_{tR}$, which are 5 g∠0° as in Table 4 in FIG. 13.

$$\{W_{cL} W_{cR}\}=\theta W_{tL}+\phi W_{rT}=\{2.6\text{ g}\angle 345° \ 2.4\text{ g}\angle 348°\} \quad (22)$$

Here, the correction weights $W_{cL}$ and $W_{cR}$ and the residual unbalance amounts are in a positional relationship having point-symmetry with respect to the rotational axis C40 of the roller 40. Therefore, the residual unbalance amounts and the unbalance positions are represented as follows.

$$\{W_{rL} W_{rR}\}\{2.6\text{ g}\angle 165° \ 2.4\text{ g}\angle 168°\} \quad (23)$$

That is, it is determined that the L-side residual unbalance amount is 2.6 g and the L-side unbalance position is 165°, and the R-side residual unbalance amount is 2.4 g and the R-side unbalance position is 168°.

Other Embodiments

Though the embodiment of the present invention is described above, the present invention is not limited to this embodiment, but alterations as follows are possible.

In the embodiment described above, the dynamic balance correction is performed so that the sum of the values of balance quality is 6 or less for both the cutter roller 20 and the anvil roller 40. The present invention is not limited to this. For example, it is possible that only one roller 20 (40) undergoes the dynamic balance correction and meets the requirement of being 6 or less and that the other roller 40 (20) does not meet the requirement. This case is also included in the scope of the present invention because having the roller that meets the requirement of being 6 or less makes it possible to achieve an appropriate amount of life extension.

Although the cutter roller 20 includes the bearers 25 in the embodiment described above, the bearers 25 are not essential components. That is, the cutter roller 20 does not have to include the bearers 25.

In the embodiment described above, the disposable diaper 1 worn by a wearer to absorb liquid excretion from the wearer was used as an example of the absorbent article. The absorbent article is not limited to this, as long as it absorbs liquid excretion such as urea and menstrual blood. For example, it may be a sanitary napkin, a pet pad that absorbs liquid excretion of pets, etc.

LIST OF REFERENCE NUMERALS

1 Diaper (Absorbent article, Product), 1a Semi-finished product (workpiece), 1h Leg opening,
10 Cutter apparatus, 12 Bearing member, 14 Bearing member,
15 Housing member, 15a Frame member, 17 Hydraulic cylinder,
20 Cutter roller, 20s Outer circumferential surface, 21 Cutter blade,
22 Roll-body section, 22a End face, 23 Small-diameter section,
25 Bearer,
40 Anvil roller, 40s Outer circumferential surface,
42 Roll-body section, 42a End face, 43 Small-diameter section,
45 Air vent, 47 Air flow path,
50 Balance weight, 50h Through hole, 57 Hole (dynamic-balance correction section),
60 Drive mechanism, 61 Coupling, 63 Drive transmission gear,
70 Collection mechanism, 72 Air suction/discharge drum,
91 Soft support bearing, 93 Vibrometer,
101 Transport roller,
122 Shaft (core section), 124 Surface-layer section,
124a Sleeve, 124b Sleeve, 124c Ring member,
142 Shaft (core section), 144 Surface-layer section,
144a Sleeve, 144b Sleeve, 144c Ring member,
A21 Cutter blade-defining area (closed area), A45 Air-vent arrangement area,
C20 Rotational axis, C40 Rotational axis, C50 Center of circle,
P20 Reference position, P40 Reference position

The invention claimed is:

1. A cutter apparatus for cutting a workpiece of an absorbent article that is being transported in a transport direction, comprising:
    a cutter roller that has a cutter blade projecting from an outer circumferential surface of the cutter roller;
    an anvil roller that receives the cutter blade on an outer circumferential surface of the anvil roller disposed to face the outer circumferential surface of the cutter roller,
    the cutter roller and the anvil roller cutting the workpiece by allowing the workpiece to pass between the cutter roller and the anvil roller while the cutter roller and the anvil roller are both rotating in the transport direction; and
    a dynamic-balance correction section that, for at least one roller of the cutter roller and the anvil roller, corrects the dynamic balance of the at least one roller so that a sum of values of balance quality at one end and another end of the at least one roller in a rotational-axis direction is 6 mm/sec or less, the balance quality being defined in JIS B 0905, wherein
    the cutter roller includes a roller-body section having two ends with respective end faces, and small-diameter sections that are formed coaxially and project at both ends of the roller-body section,
    bearers are respectively provided on both end portions of the roller-body section, and are pressed against the anvil roller, the cutter apparatus includes balance weights, respective through holes are formed at respective center portions of the respective balance weights, the balance weights are respectively placed on both end faces of the roller-body section such that the small-diameter sections are respectively fitted into the through holes, the balance weights abut against the end faces, and balancing holes corresponding to the dynamic-balance correction section are formed in the balance weights, whereby the dynamic balance is corrected.

2. The cutter apparatus for a workpiece of an absorbent article according to claim 1, wherein
    the apparatus further comprises
    a dynamic-balance correction section that, for both of the cutter roller and the anvil roller, corrects the dynamic balance of one or both of the rollers so that the sum of values of balance quality at one end and another end of each of the rollers in the rotational-axis direction is 6 mm/sec or less, the balance quality being defined in JIS B 0905.

3. The cutter apparatus for a workpiece of an absorbent article according to claim 1, wherein
    the cutter roller and the anvil roller are arranged vertically,
    a rotational direction in which the cutter roller rotates about the rotational axis of the cutter roller is opposite to a rotational direction in which the anvil roller rotates about the rotational axis of the anvil roller,
    both the cutter roller and the anvil roller have their respective predetermined reference positions facing each other on their respective outer circumferential surfaces,
    positions on each of the cutter roller and the anvil roller along their respective rotational direction corresponds to 0° to 360° rotational-angular positions from their respective start positions which are the predetermined reference positions,
    when cutting the workpiece by allowing the workpiece to pass between the cutter roller and the anvil roller, the cutter roller and the anvil roller are rotated so that their rotational-angular positions match with each other,
    the values of the balance quality at the one end and the other end are calculated based on residual unbalance amounts measured using a two-plane balancing machine defined in JIS B 7737, and
    assuming that the one of the cutter roller and the anvil roller is a first roller and the other roller is a second roller,
    both an unbalance position related to the residual unbalance amount at one end of the first roller and an unbalance position related to the residual unbalance amount at the other end of the first roller fall within a range of 90° to 270° rotational-angular positions, and
    both an unbalance position related to the residual unbalance amount at one end of the second roller and an unbalance position related to the residual unbalance amount at the other end of the second roller fall within a range of 270° to 360° or 0° to 90° rotational-angular positions.

4. The cutter apparatus for a workpiece of an absorbent article according to claim 1, wherein
    the roller whose dynamic balance is to be corrected has a surface-layer section and a core section that is located more inside than the surface-layer section, the surface-layer section and the core section being made of different materials from each other,
    a hardness of the surface-layer section is higher than a hardness of the core section, and
    an end face of the core section in a direction along the rotational axis has a balancing hole that serves as the dynamic-balance correction section, and
    the dynamic balance of the roller is corrected by forming the balancing hole.

5. The cutter apparatus for a workpiece of an absorbent article according to claim 4, wherein
    the cutting of the workpiece is to punch a part of the workpiece into a predetermined punched shape,
    the cutter blade defines a closed area on the outer circumferential surface of the cutter roller in correspondence with the punched shape,
    the roller whose balance is corrected by forming a balancing hole on an end face thereof is the anvil roller,
    the anvil roller has a plurality of air vents for suction on an area of the outer circumferential surface of the anvil roller, the area facing the closed area of the cutter blade, and
    the anvil roller has an air flow path inside the anvil roller along the rotational axis so that an end face at one end of the anvil roller is connected to the air vents, the air flow path communicating with the air vents and sucking air from the air vents.

6. The cutter apparatus for a workpiece of an absorbent article according to claim 1, wherein the dynamic-balance correction section includes a balancing hole in the at least one roller.

7. The cutter apparatus for a workpiece of an absorbent article according to claim 1, wherein the cutter blade is located asymmetrically with respect to the rotational axis of the cutter roller, and the dynamic-balance correction section is part of the cutter roller.

8. The cutter apparatus for a workpiece of an absorbent article according to claim 1, wherein the anvil roller includes air vents and air flow paths formed asymmetrically with respect to the rotational axis of the anvil roller, and the dynamic-balance correction section is part of the anvil roller.

9. A cutter apparatus for cutting a workpiece of an absorbent article that is being transported in a transport direction, comprising:

a cutter roller that has a cutter blade projecting from an outer circumferential surface of the cutter roller;

an anvil roller that receives the cutter blade on an outer circumferential surface of the anvil roller disposed to face the outer circumferential surface of the cutter roller, the cutter roller and the anvil roller cutting the workpiece by allowing the workpiece to pass between the cutter roller and the anvil roller while the cutter roller and the anvil roller are both rotating in the transport direction; and a dynamic-balance correction section configured such that, for at least one roller of the cutter roller and the anvil roller, the correction section corrects the dynamic balance of the at least one roller so that a sum of values of balance quality at one end and another end of the at least one roller in a rotational-axis direction is 6 mm/sec or less, the balance quality being defined in JIS B 0905, wherein the dynamic-balance correction section includes a hole in the at least one roller, wherein the cutter roller includes a roller-body section having two ends with respective end faces, and small-diameter sections that are formed coaxially and project at both ends of the roller-body section, bearers are respectively provided on both end portions of the roller-body section, and are pressed against the anvil roller, the cutter apparatus includes balance weights, respective through holes are formed at respective center portions of the respective balance weights, the balance weights are respectively placed on both end faces of the roller-body section such that the small-diameter sections are respectively fitted into the through holes, the balance weights abut against the end faces, and balancing holes corresponding to the dynamic-balance correction section are formed in the balance weights, whereby the dynamic balance is corrected.

10. The cutter apparatus for a workpiece of an absorbent article according to claim 9, wherein the cutter blade is located asymmetrically with respect to the rotational axis of the cutter roller, and the dynamic-balance correction section is part of the cutter roller.

11. The cutter apparatus for a workpiece of an absorbent article according to claim 9, wherein the anvil roller includes air vents and air flow paths formed asymmetrically with respect to the rotational axis of the anvil roller, and the dynamic-balance correction section is part of the anvil roller.

* * * * *